(12) United States Patent
Arrigo

(10) Patent No.: US 9,901,367 B2
(45) Date of Patent: Feb. 27, 2018

(54) SAFETY SCALPEL

(71) Applicant: Spectra Medical Devices, Inc., Wilmington, MA (US)

(72) Inventor: Anthony C. Arrigo, North Andover, MA (US)

(73) Assignee: SPECTRA MEDICAL DEVICES, INC., Wilmington, DE (US)

( * ) Notice: Subject to any disclaimer, the term of this patent is extended or adjusted under 35 U.S.C. 154(b) by 0 days.

(21) Appl. No.: 15/123,465

(22) PCT Filed: Mar. 4, 2015

(86) PCT No.: PCT/US2015/018722
§ 371 (c)(1),
(2) Date: Sep. 2, 2016

(87) PCT Pub. No.: WO2015/134601
PCT Pub. Date: Sep. 11, 2015

(65) Prior Publication Data
US 2017/0071619 A1    Mar. 16, 2017

Related U.S. Application Data

(60) Provisional application No. 61/948,383, filed on Mar. 5, 2014.

(51) Int. Cl.
*A61B 17/00* (2006.01)
*A61B 17/3211* (2006.01)
(Continued)

(52) U.S. Cl.
CPC ............ *A61B 17/3211* (2013.01); *A61B 2017/320052* (2013.01); *A61B 2017/320064* (2013.01);
(Continued)

(58) Field of Classification Search
CPC .......... A61B 17/3211; A61B 2090/061; A61B 2017/320064; A61B 2017/320052; A61B 2017/32113
See application file for complete search history.

(56) References Cited

U.S. PATENT DOCUMENTS 5,116,351 A * 5/1992 Frassetti ............ A61B 17/3211
30/161
5,292,329 A * 3/1994 Werner .............. A61B 17/3211
30/162

(Continued)

OTHER PUBLICATIONS

International Search Report in PCT/US2015/018722 dated May 27, 2015, 2 pages.
(Continued)

*Primary Examiner* — Sean Michalski
(74) *Attorney, Agent, or Firm* — Foley & Lardner LLP

(57) ABSTRACT

A scalpel may include a blade cover having a length within the range of 3 to 9 centimeters and a blade body having a blade carrier and a blade. The blade cover may include a housing, a front lock member, a back lock member, and a safety lock member. The blade body may be fully retractable and movable within the housing. The front lock member, the back lock member, and the safety lock member may be configured to define at least three different locked positions of the blade body relative to the housing.

7 Claims, 23 Drawing Sheets

(51) Int. Cl.
  *A61B 17/32* (2006.01)
  *A61B 90/00* (2016.01)
(52) U.S. Cl.
  CPC ............... *A61B 2017/32113* (2013.01); *A61B 2090/061* (2016.02)

(56) References Cited

U.S. PATENT DOCUMENTS

| | | | | |
|---|---|---|---|---|
| 5,299,357 A * | 4/1994 | Wonderley | ......... | A61B 17/3211 30/320 |
| 5,330,492 A * | 7/1994 | Haugen | ............ | A61B 17/3211 30/151 |
| 5,330,493 A | 7/1994 | Haining | | |
| 5,342,379 A * | 8/1994 | Volinsky | ............ | A61B 17/3213 30/162 |
| 5,344,424 A | 9/1994 | Roberts et al. | | |
| 5,417,704 A * | 5/1995 | Wonderley | ......... | A61B 17/3211 30/162 |
| 5,431,672 A | 7/1995 | Cote et al. | | |
| 5,481,804 A | 1/1996 | Platts | | |
| 5,599,351 A * | 2/1997 | Haber | ................ | A61B 17/3211 30/151 |
| 5,620,454 A * | 4/1997 | Pierce | .................... | A61B 17/32 30/162 |
| 5,683,407 A * | 11/1997 | Jolly | .................. | A61B 17/3213 606/172 |
| 5,779,724 A * | 7/1998 | Werner | .............. | A61B 17/3211 30/162 |
| 5,868,771 A | 2/1999 | Herbert et al. | | |
| 6,254,621 B1 * | 7/2001 | Shackelford | ....... | A61B 17/3213 30/162 |
| 6,589,258 B2 * | 7/2003 | Pilo | .................... | A61B 17/3213 606/167 |
| 6,626,925 B2 * | 9/2003 | Newman | ............ | A61B 17/3213 30/151 |
| D490,153 S * | 5/2004 | Montgomery | ..... | A61B 17/3213 D24/128 |
| 7,153,317 B2 * | 12/2006 | Kanodia | ............ | A61B 17/3211 30/162 |
| 7,156,231 B1 * | 1/2007 | Austria | .................. | A61B 17/32 206/355 |
| 7,207,999 B2 * | 4/2007 | Griffin | ............... | A61B 17/3213 606/167 |
| 7,810,241 B2 * | 10/2010 | Pooler | ................ | A61B 17/3211 30/151 |
| RE42,507 E * | 6/2011 | Wilkinson | ......... | A61B 17/3213 30/151 |
| 8,114,103 B2 * | 2/2012 | Rasco | ............... | A61B 17/3213 30/151 |
| 8,464,430 B2 * | 6/2013 | Cote | .................. | A61B 17/3211 30/162 |
| 8,931,181 B2 * | 1/2015 | Milton | ............... | A61B 17/3213 30/162 |
| 8,959,778 B2 * | 2/2015 | Baid | .................. | A61B 17/3213 30/151 |
| 2003/0093905 A1 * | 5/2003 | Dambal | ............. | A61B 17/3211 30/162 |
| 2004/0098001 A1 * | 5/2004 | Holman | ............. | A61B 17/3213 606/167 |
| 2004/0186496 A1 | 9/2004 | Sandel et al. | | |
| 2004/0236359 A1 * | 11/2004 | Shi | ..................... | A61B 17/3213 606/167 |
| 2005/0021064 A1 * | 1/2005 | Lee | .................... | A61B 17/3211 606/167 |
| 2006/0095057 A1 * | 5/2006 | Yi | ...................... | A61B 17/3213 606/167 |
| 2008/0249550 A1 * | 10/2008 | Djordjevic | ......... | A61B 17/3213 606/167 |
| 2009/0192538 A1 * | 7/2009 | Sandel | ............... | A61B 17/3213 606/167 |
| 2010/0036404 A1 * | 2/2010 | Yi | ...................... | A61B 17/3213 606/167 |
| 2010/0168773 A1 * | 7/2010 | Funderburk | ....... | A61B 17/3213 606/167 |
| 2010/0268258 A1 * | 10/2010 | Maxwell | ............ | A61B 17/3213 606/167 |
| 2012/0083816 A1 * | 4/2012 | Hajgato | ............. | A61B 17/3213 606/170 |
| 2012/0215241 A1 * | 8/2012 | Trees | .................. | A61B 17/3211 606/167 |
| 2012/0245610 A1 * | 9/2012 | Hajgato | ............. | A61B 17/3213 606/167 |
| 2012/0259352 A1 * | 10/2012 | Rosenhan | .......... | A61B 17/0467 606/167 |
| 2013/0158574 A1 * | 6/2013 | Yi | ...................... | A61B 17/3213 606/167 |
| 2014/0157604 A1 * | 6/2014 | George | ............. | A61B 17/3211 30/151 |
| 2014/0208596 A1 * | 7/2014 | Constantine | .............. | B26B 1/08 30/162 |
| 2015/0265360 A1 * | 9/2015 | Tatewaki | ............ | A61B 19/44 235/375 |
| 2017/0189048 A1 * | 7/2017 | Kanodia | ............ | A61B 17/3211 |

OTHER PUBLICATIONS

Written Opinion of the International Searching Authority in PCT/US2015/018722 dated May 27, 2015, 5 pages.
International Preliminary Report on Patentability and Transmittal received in corresponding International Application No. PCT/US2015/018722, dated Sep. 15, 2016, 7 pages.

* cited by examiner

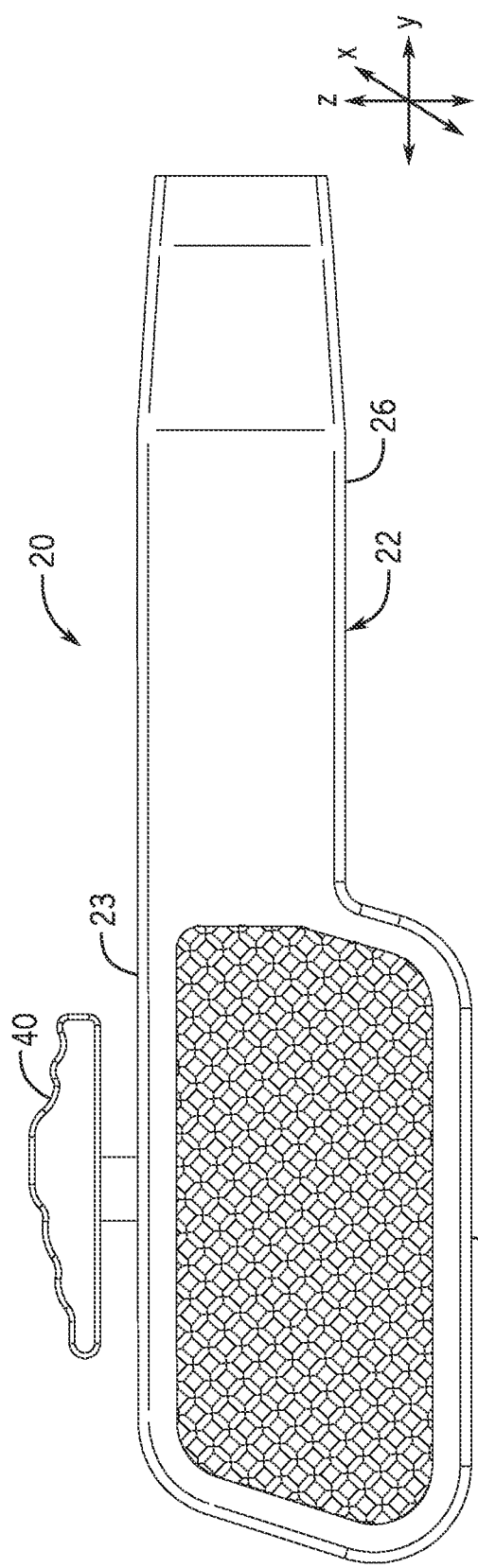
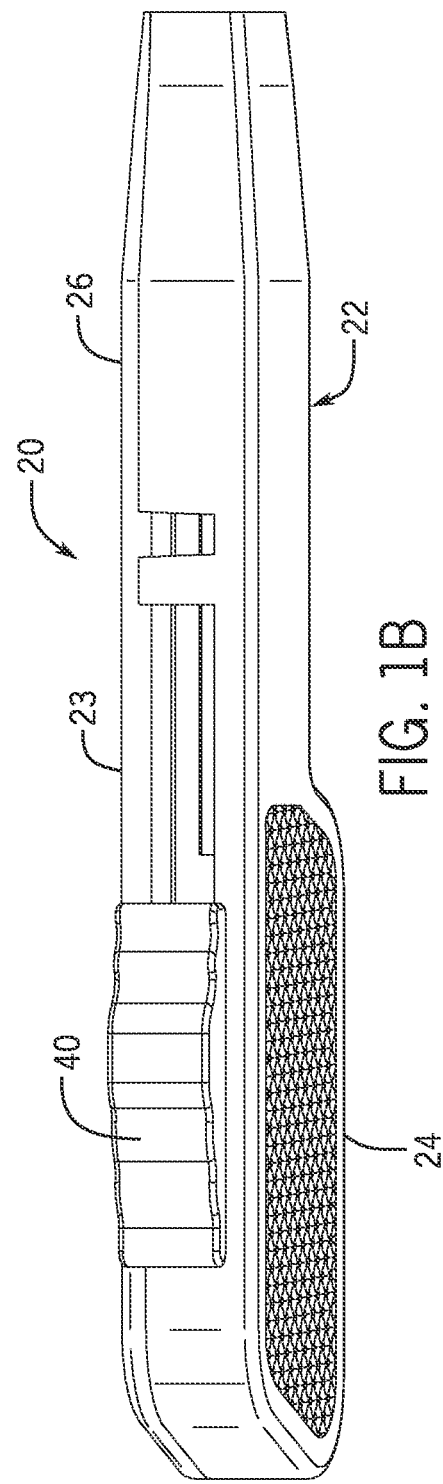
FIG. 1A
FIG. 1B

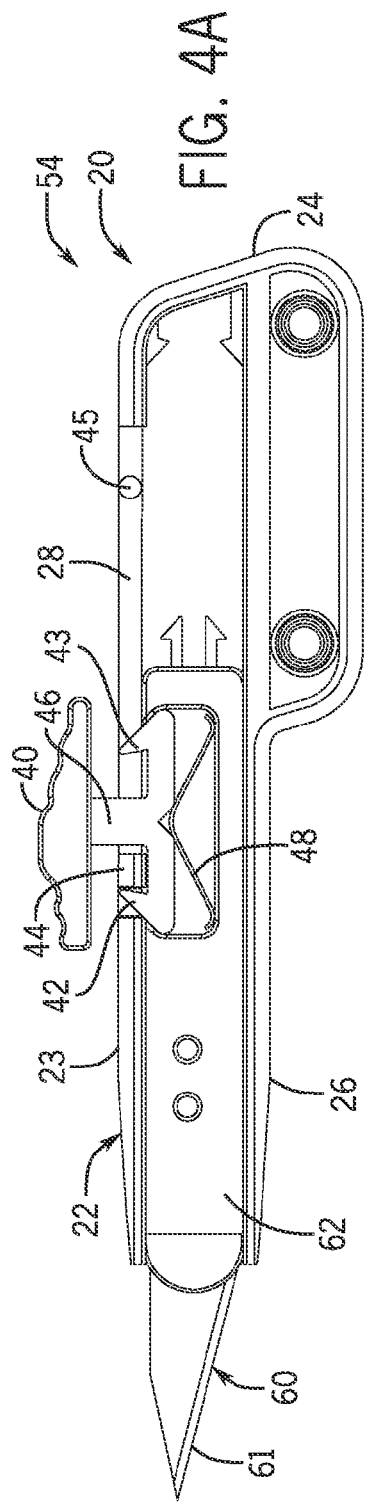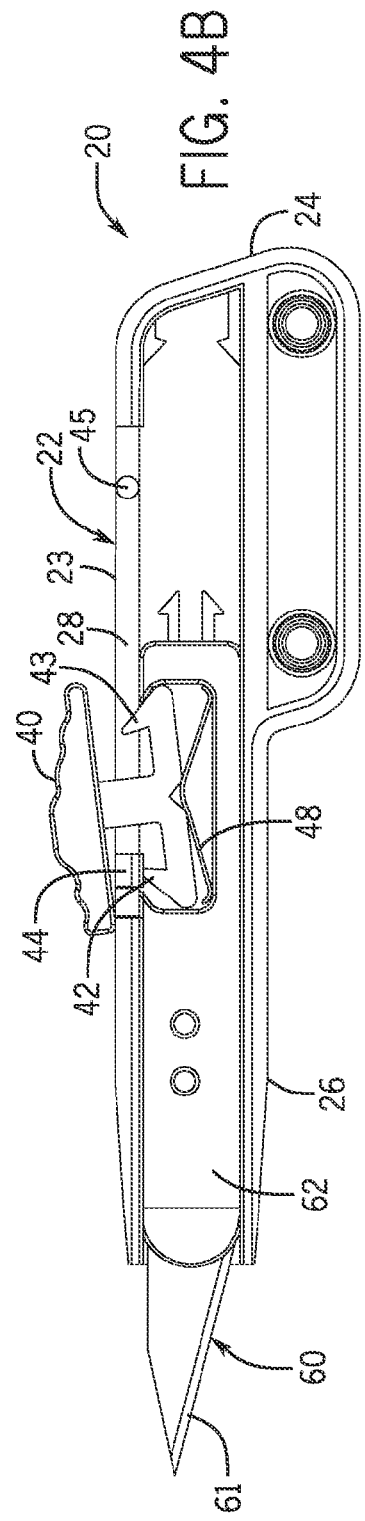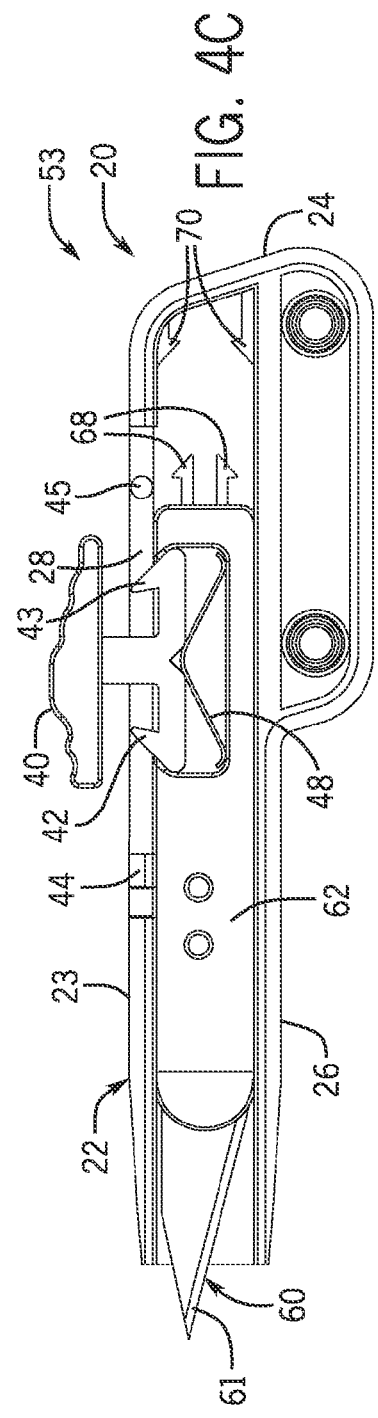

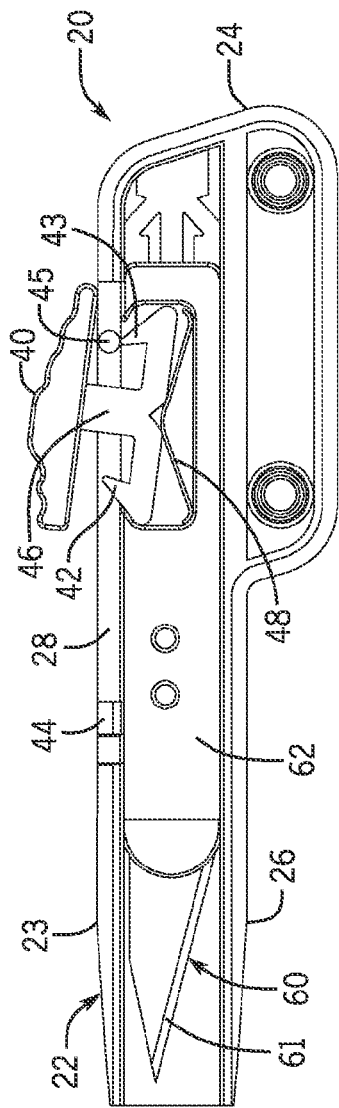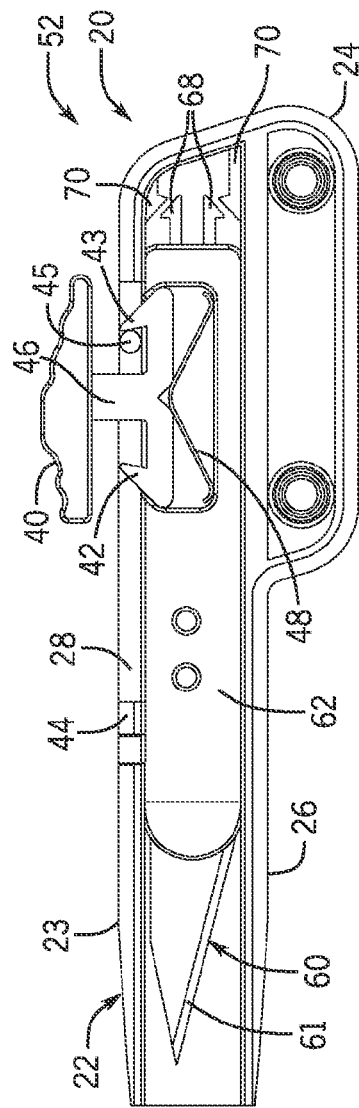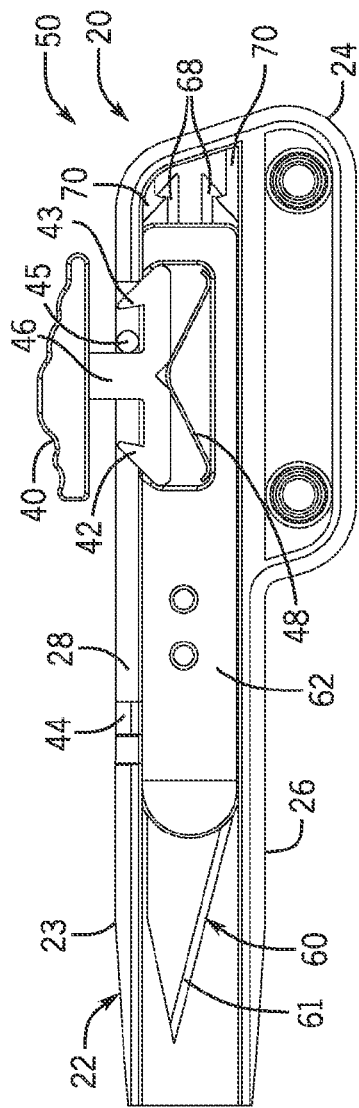

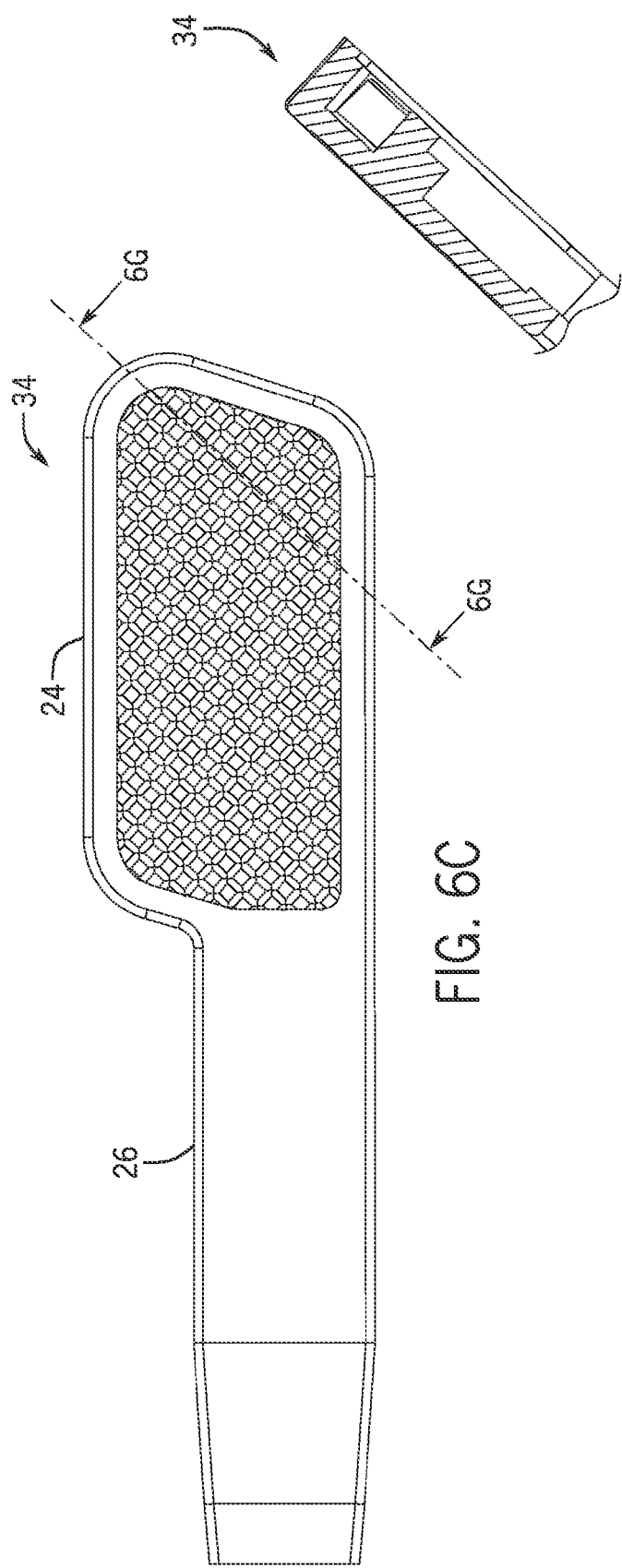
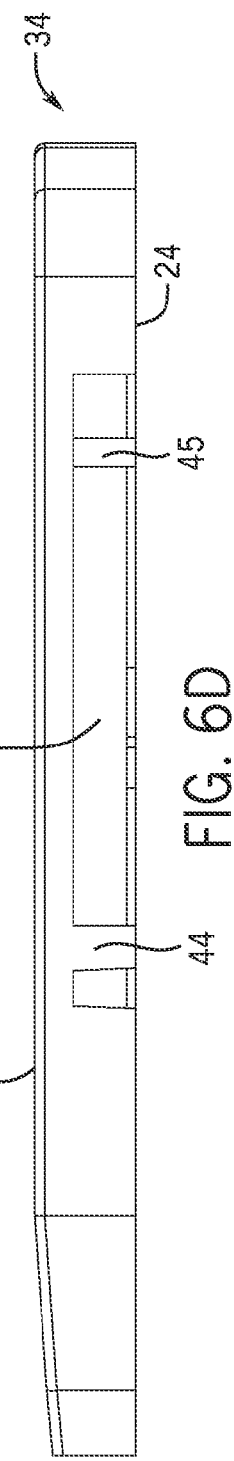
FIG. 6C
FIG. 6D
FIG. 6G

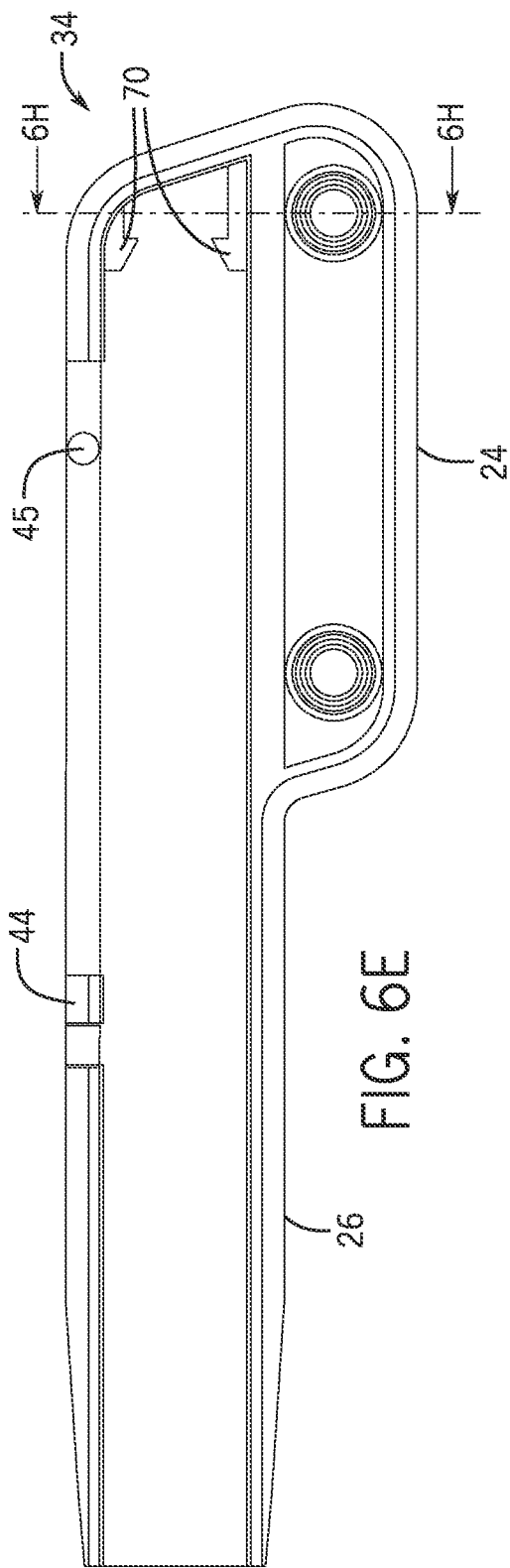
FIG. 6E
FIG. 6F
FIG. 6H

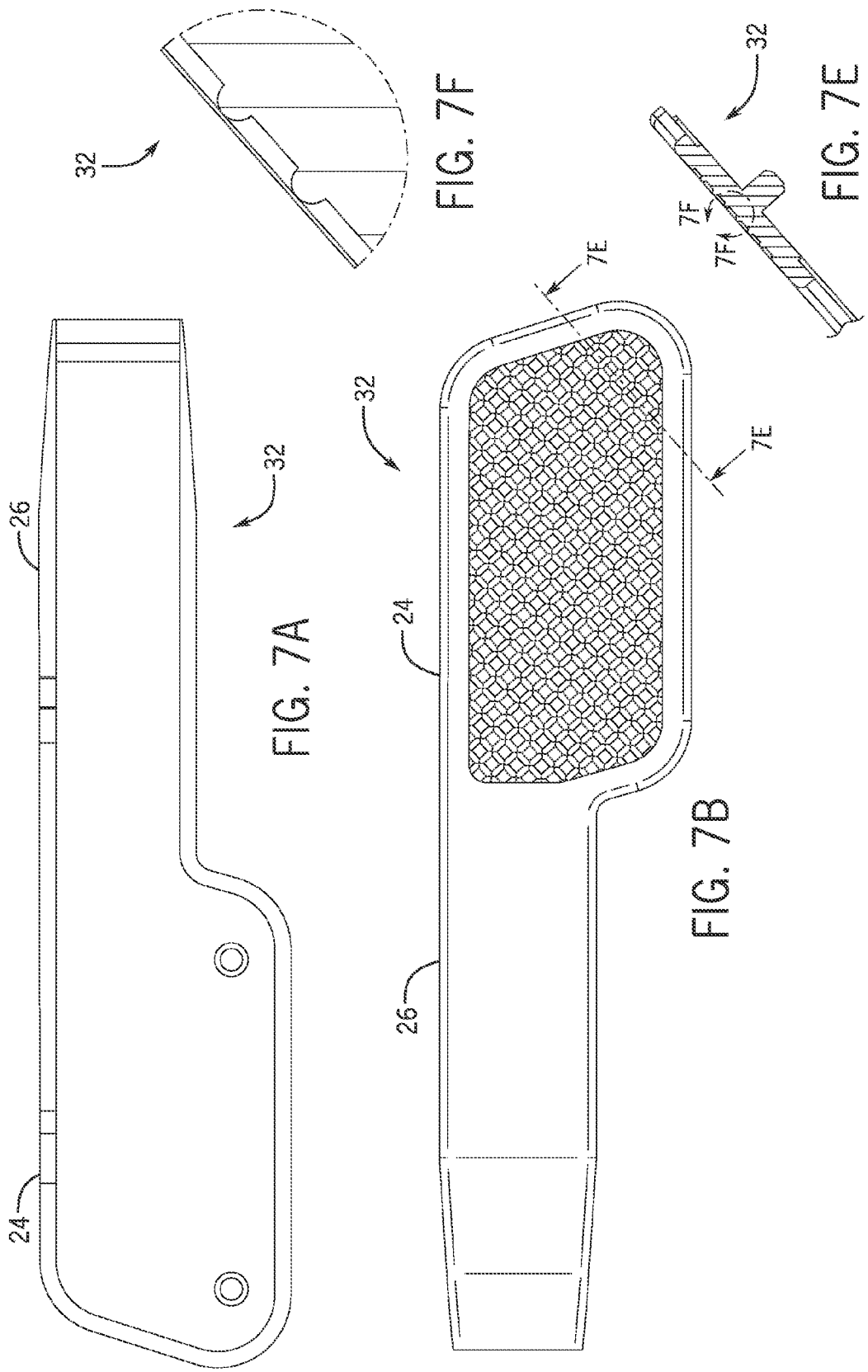

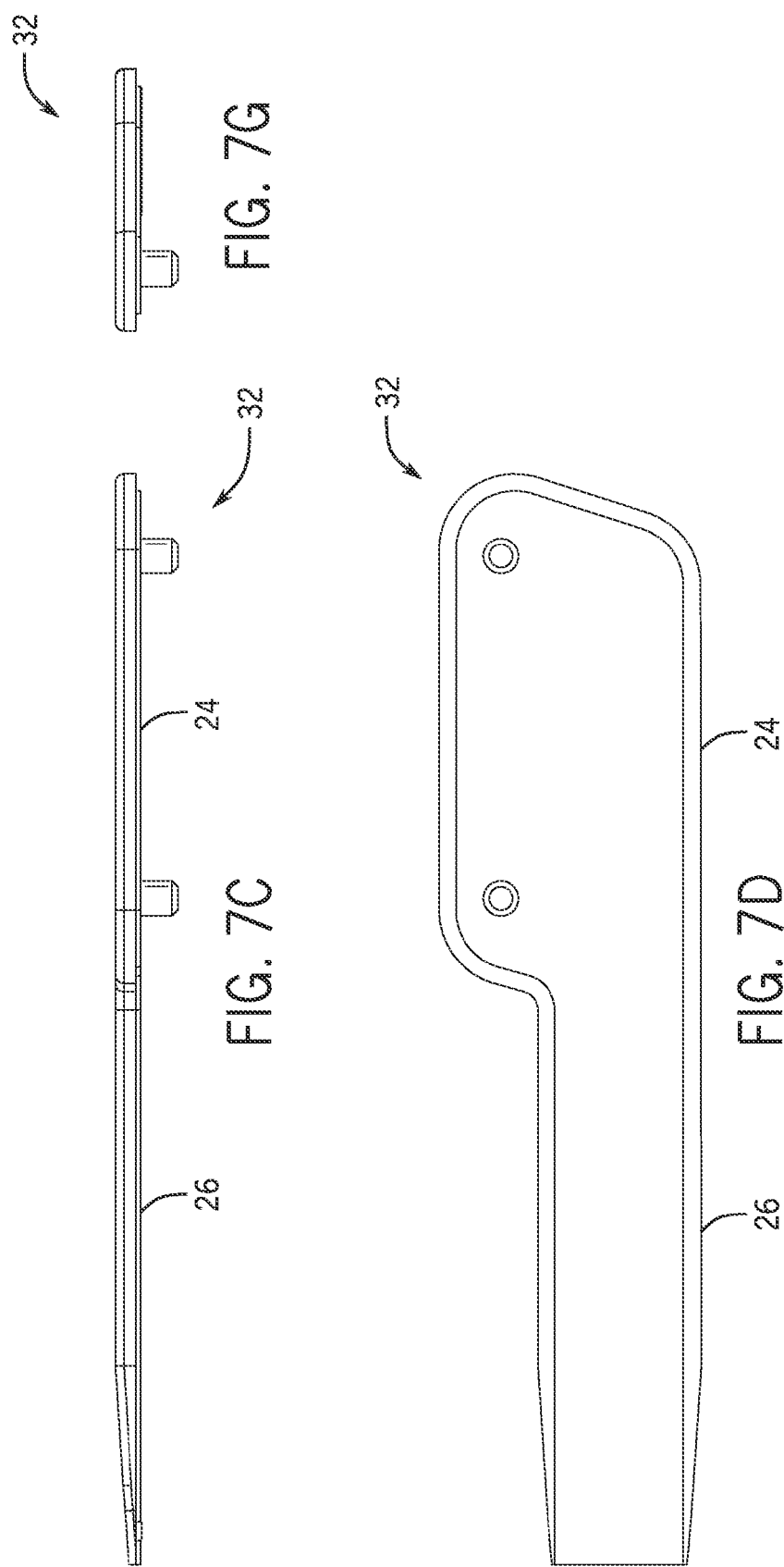

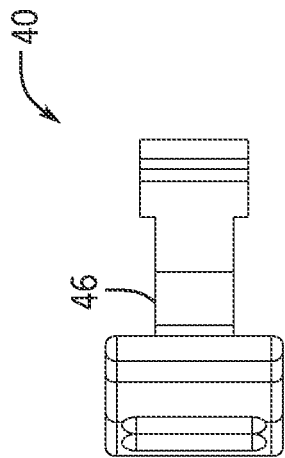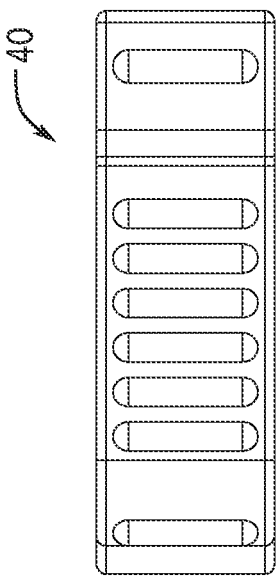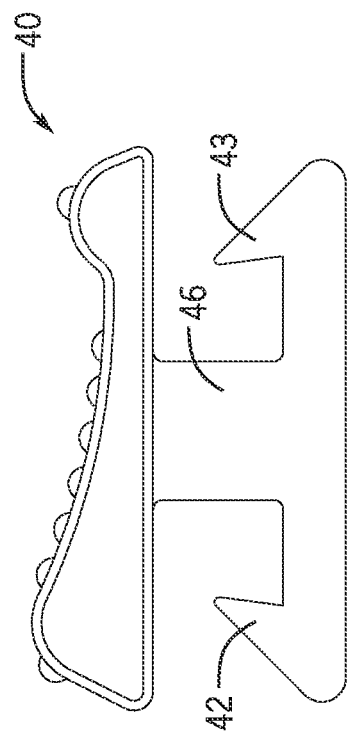
FIG. 9C
FIG. 9B
FIG. 9A

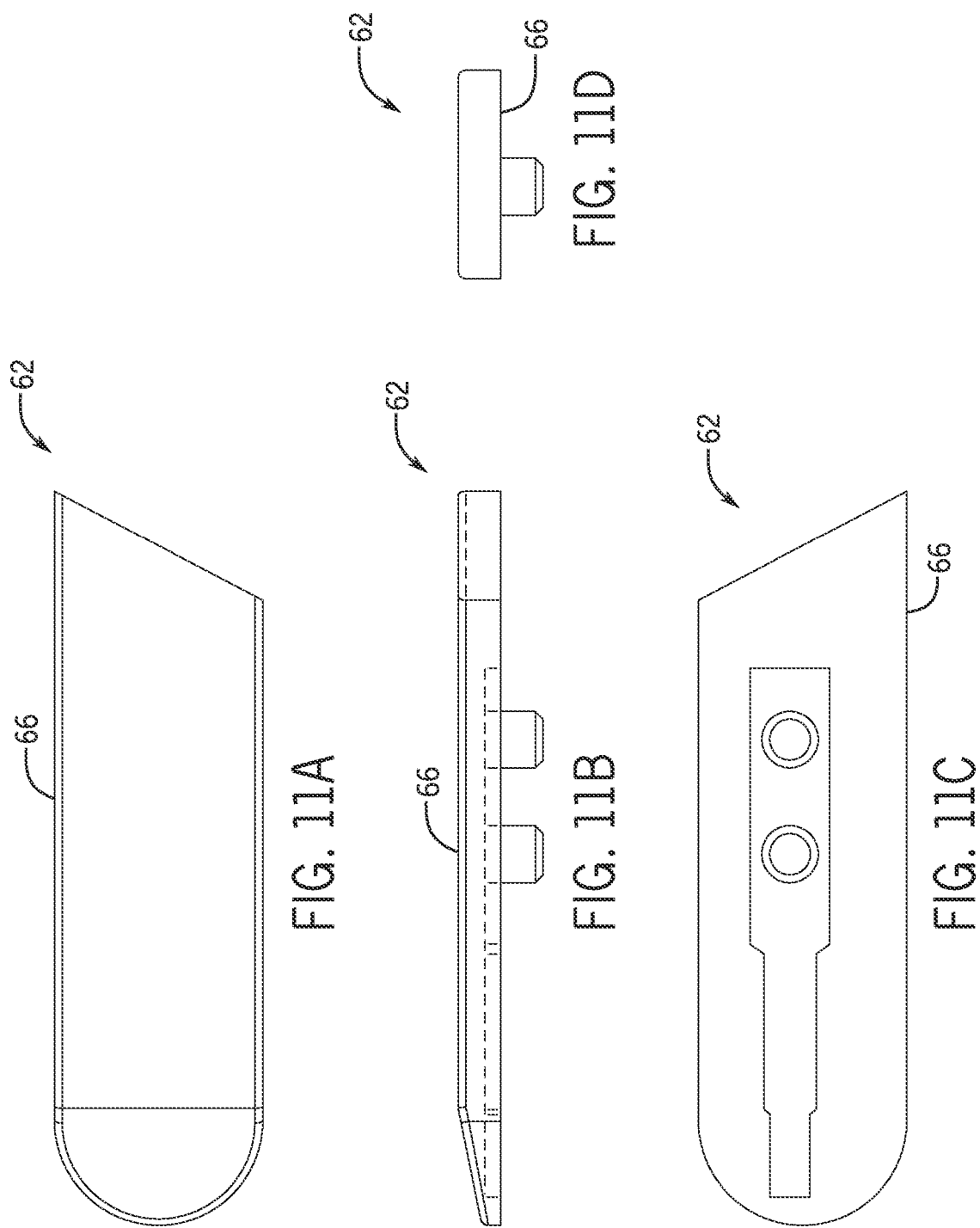

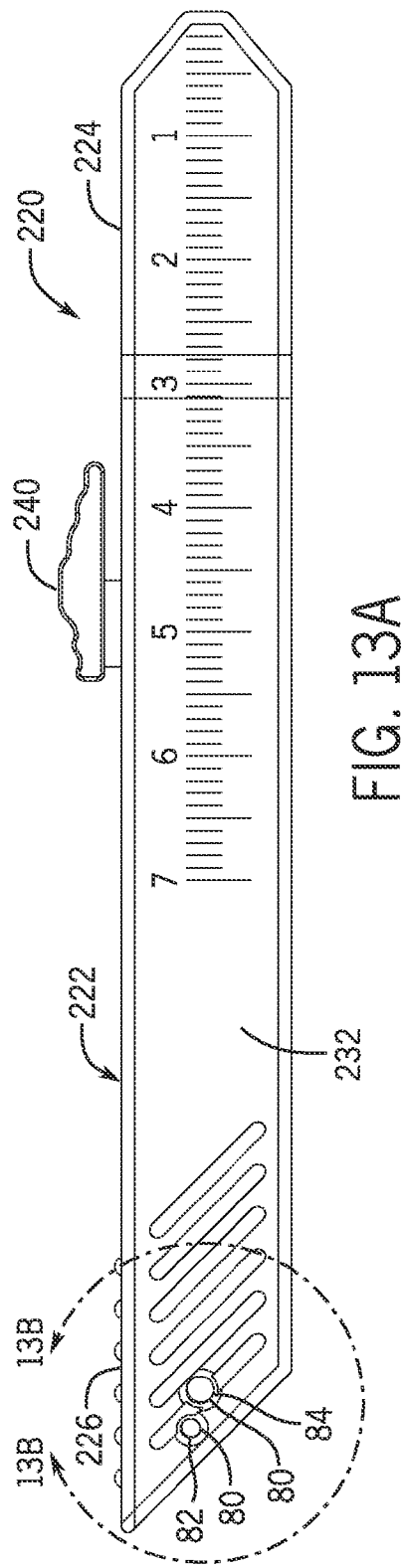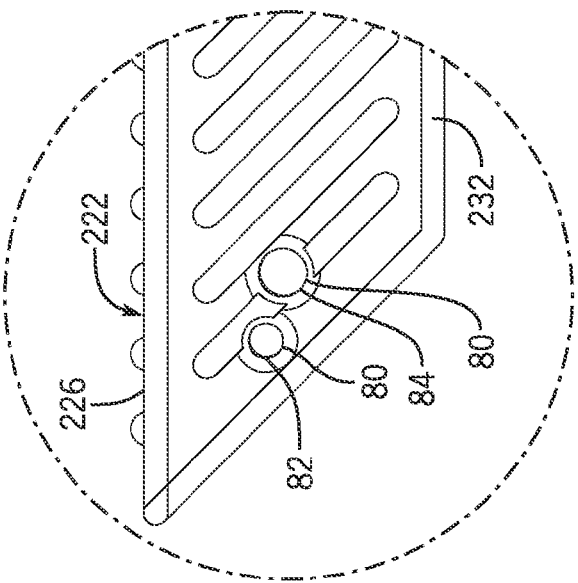

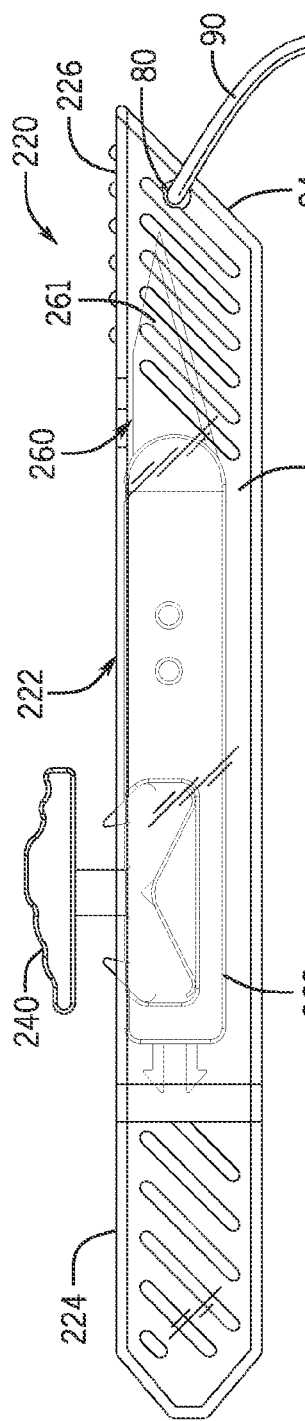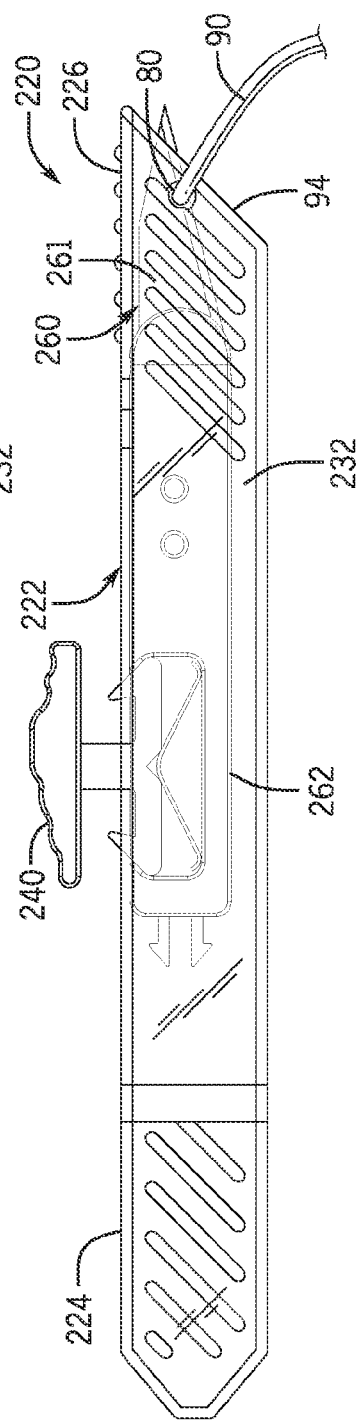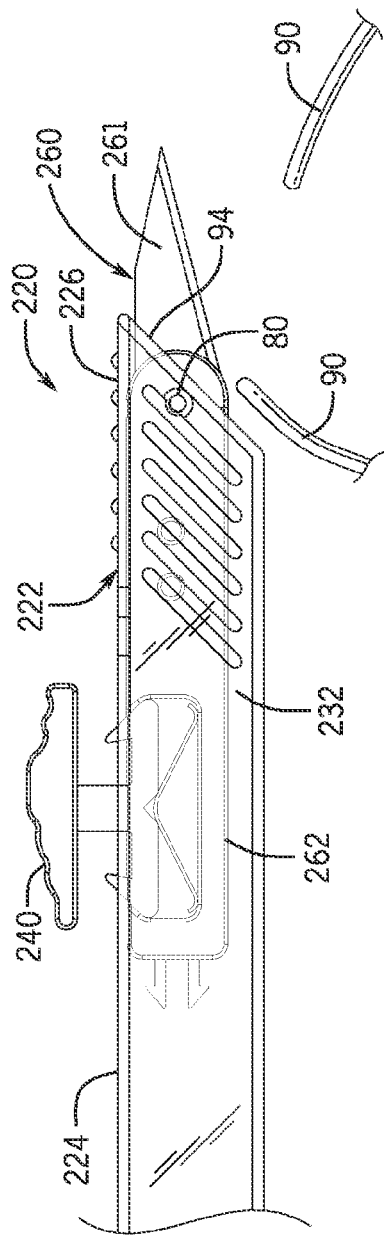

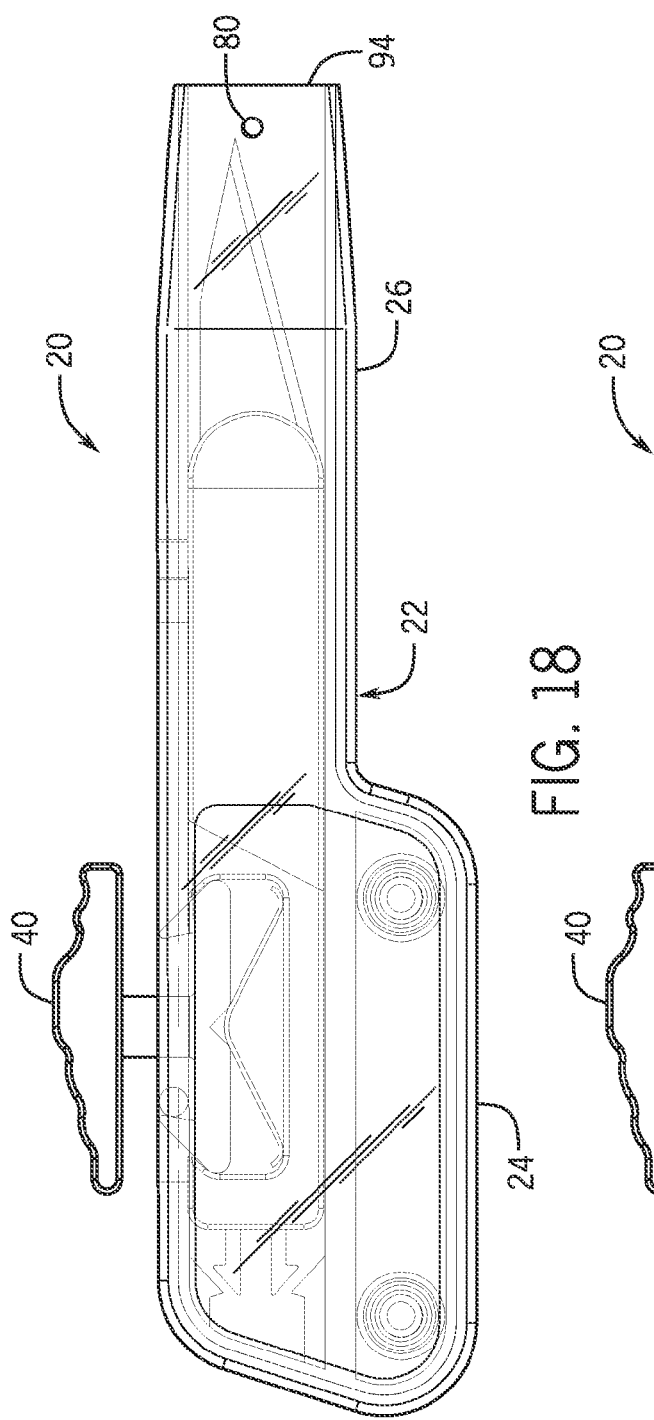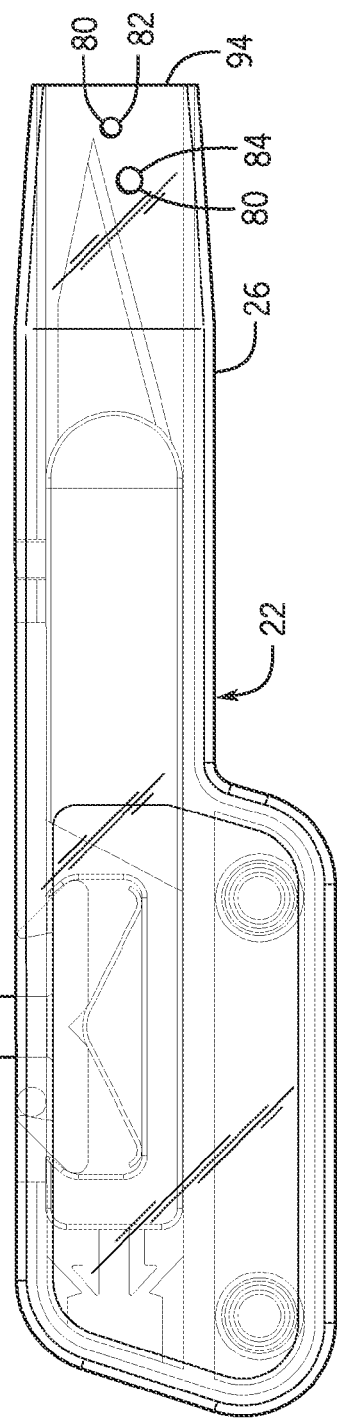

SAFETY SCALPEL

RELATED PATENT APPLICATIONS

The present application is a U.S. National Stage of International Application No. PCT/US2015/018722 filed on Mar. 4, 2015, which claims the benefit of U.S. Provisional Patent Application No. 61/948,383 filed on Mar. 5, 2014, the entire disclosures of all of which are incorporated herein by reference.

FIELD

The disclosure relates generally to scalpels.

BACKGROUND

Generally, a scalpel includes a handle with a sharp blade attached. Scalpels may be used within a variety of different settings, including medical settings such as an operating room or hospital. For example, scalpels may be used as cutting instruments for surgeries.

Although the sharp blade of a scalpel is an essential component to many surgeries, the exposed, sharp blade may also pose a threat to the user or nearby people, such as the surgeon, the support personnel, or the patient. For example, the blade may result in unintentional cuts, puncture wounds, and/or tears (in the surgical gloves) before, after, or during procedures, all of which may further result in potentially life-threatening contamination or infection. For example, a used blade of the scalpel may be contaminated or infected, which may spread to other people if they are cut by the exposed blade. Even people outside of the operating room, such as personnel in charge of sanitation or disposal, may also be at risk due to exposed blades. This may be prevented with safety mechanisms.

A lid or cap may be used with the scalpel to reduce the risk of injury. However, the lid or cap may easily be lost or misplaced during surgery. Further, a lid or cap requires the surgeon to use both hands to remove from or place on the scalpel.

It may be desirable to use a mini scalpel instead of normal sized or larger scalpels for a variety of reasons, such as surgical procedures that require small instruments due to narrow operating fields or limited space within the operating room or on the surgical tray or table.

SUMMARY

According to one embodiment, a scalpel may include a blade cover having a length within the range of 3 to 9 centimeters and a blade body having a blade carrier and a blade. The blade cover may include a housing, a front lock member, a back lock member, and a safety lock member. The blade body may be fully retractable and movable within the housing. The front lock member, the back lock member, and the safety lock member may be configured to define at least three different locked positions of the blade body relative to the housing.

According to another embodiment, a safety scalpel may comprise a blade cover including a housing having a first side with a first hole and a second side with a second hole and a blade body having a blade carrier and a blade. The blade body may be fully retractable and movable within the housing along a longitudinal axis. The first hole and the second hole may be disposed on a common center axis that is substantially perpendicular to the longitudinal axis of the blade body and intersects with a path of movement of the blade such that the blade is configured to cut a structure extending through the first and second holes as the blade is extended toward a use position.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Features, aspects, and advantages of the present invention will become apparent from the following description, appended claims, and the accompanying exemplary embodiments shown in the drawings, which are briefly described below.

FIG. 1A is a front view of a mini safety scalpel according to one embodiment in a stowed position.

FIG. 1B is a top view of the mini scalpel of FIG. 1A.

FIGS. 4A-4F are cut away, front views of the mini scalpel of FIG. 1A moving from a stowed position to a safety position.

FIG. 6C is an outside, back view of the back side of the mini scalpel of FIG. 1A.

FIG. 6D is a top view of the back side of the mini scalpel of FIG. 1A.

FIG. 6E is an inside, front view of the back side of the mini scalpel of FIG. 1A.

FIG. 6F is a right side view of the back side of the mini scalpel of FIG. 1A.

FIG. 6G is a cross sectional view of Section 6G-6G of FIG. 6C.

FIG. 6H is a cross sectional view of Section 6H-6H of FIG. 6E.

FIG. 7A is an inside, front view of a front side of the mini scalpel of FIG. 1A.

FIG. 7B is an outside, back view of the front side of the mini scalpel of FIG. 1A.

FIG. 7C is a bottom view of the front side of the mini scalpel of FIG. 1A.

FIG. 7D is an inside, front view of the front side of the mini scalpel according to one embodiment.

FIG. 7E is a cross sectional view of Section 7E-7E of FIG. 7B.

FIG. 7F is a detail view of Section 7F of FIG. 7E.

FIG. 7G is a side view of the mini scalpel of FIG. 1A.

FIG. 9A is a front view of one embodiment of a pusher that can be used within the scalpel of FIG. 1A.

FIG. 9B is a top view of the pusher of FIG. 9A.

FIG. 9C is a side view of the pusher of FIG. 9A.

FIG. 11A is an outside, front view of a blade carrier backing that can be used within the scalpel of FIG. 1A.

FIG. 11B is a top view of the blade carrier of FIG. 11A.

FIG. 11C is an inside, back view of the blade carrier backing of FIG. 11A.

FIG. 11D is a right side view of the blade carrier backing of FIG. 11A.

FIG. 13A is a front view of the long-handled scalpel of FIG. 12.

FIG. 13B is an enlarged views of Section 13B of FIG. 13A.

FIGS. 17A-17C are front views of a structure being cut in the holes of the long-handled scalpel of FIG. 14A.

FIG. 18 is a front view of a mini-scalpel according to another embodiment.

FIG. 19 is a front view of a mini-scalpel according to yet another embodiment.

DETAILED DESCRIPTION

Referring generally to the figures, disclosed herein is a miniature safety scalpel, as shown according to exemplary embodiments. The mini safety scalpel may include a blade cover and a retractable blade body. The blade cover may include a housing and the blade body may retract directly into and be movable within the housing. Additionally, the blade cover may be locked into at least three different locked positions relative to the housing, as described further herein. The blade body may be moved between the use position, the unlocked position, the stowed position, and the safety position with one hand.

Currently, in order for a doctor or surgeon to be fully protected while using a scalpel, as well as follow certain regulations or laws regarding the safety mechanisms of sharp surgical instruments, a regularly sized scalpel (e.g., a long-handled scalpel) with a safety mechanism must be used. However, it is not always desirable to use a long-handled scalpel, and instead, a mini scalpel may be desired. A mini scalpel is particularly beneficial within a variety of different applications, such as surgeries with a relatively small working area.

For example, procedural or surgical trays, such as thermoformed trays with cavities to hold surgical instruments, often include a cavity to hold a mini scalpel. This cavity may be too small to hold a regularly sized scalpel. However, since there are currently no mini scalpels with suitable safety features, the entire tray must be replaced or reconfigured in order for the doctor or surgeon to use any safety scalpels (i.e. the regularly sized scalpels with safety features), which may be costly.

Further, the doctor or surgeon may be more used to or comfortable with a mini scalpel or a particular procedure may necessitate the use of a mini scalpel. However, since there are no mini scalpels with suitable safety features, the doctors or surgeons must either use regularly sized scalpels with safety features in order to properly protect themselves and any associated people, forcing them to use a less desirable or optimal instrument and possibly reducing their performance or use mini scalpels without safety features, which may be hazardous.

Therefore, there is a need in the market for a mini scalpel with safety features. The mini safety scalpel may be used with existing trays, eliminating the need to replace the tray in order to hold long-handled scalpels. Further, the doctor or surgeon may continue to use the size scalpel they are most comfortable with, without sacrificing safety.

The Mini Safety Scalpel 20

Figure 1C:
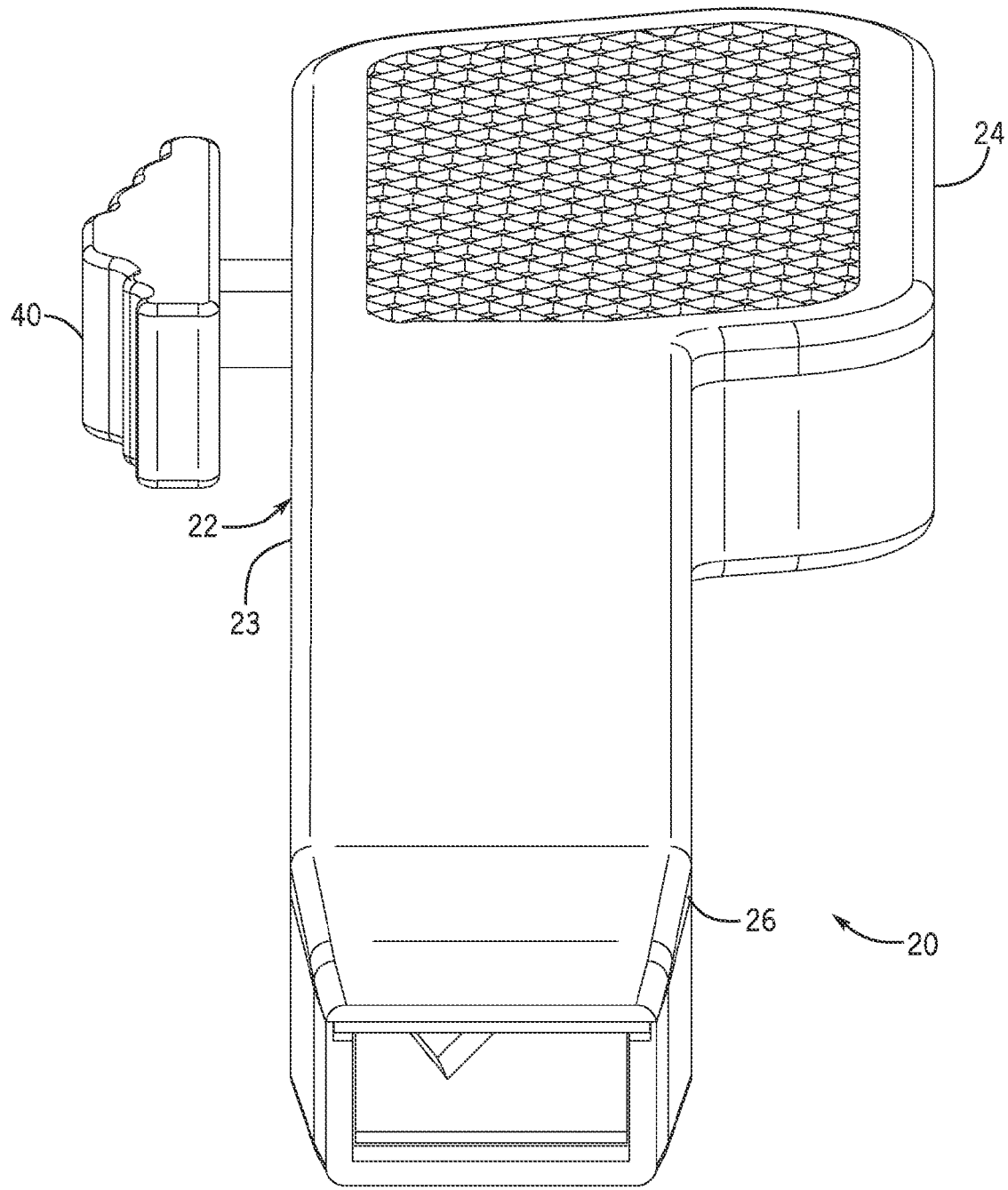
FIG. 1C is a perspective, right hand view of the mini scalpel of FIG. 1A.

FIGS. 1A-1C illustrate an exemplary embodiment of a mini safety scalpel 20. The scalpel 20 may include an outercase, body, or blade cover 22, a blade body 60, and a button, plunger, or pusher 40. The blade cover 22 may include a housing 23, a handle 24, and a shaft 26. The blade body 60 may include a blade 61 and a blade carrier 62. The pusher 40 may be used to move the blade body 60 within the blade cover 22 and may interact with the blade body 60 such that movement of the blade body 60 corresponds to movement of the pusher 40. As discussed further herein, the blade body 60 may be fully retractable into and movable within at least a portion of the housing 23 and the blade body 60 may be locked to the blade cover 22 in at least three different locked positions: the use position 54, the stowed position 52, and the safety position 50. The blade cover 22 may also include a front lock member 44, a back lock member 45, and a safety lock member 70 to define the three different locked positions of the blade body 60 relative to the housing 23 and to lock with the blade body 60.

The mini safety scalpel 20 may include a range of sizes according to the desired configuration. For example, preferably, the length of the blade cover 22 of the mini safety scalpel 20 may be between 3 and 9 cm (the length of the handle 24 may be between 1 and 4.5 cm and the length of the shaft 26 may be between 1 and 5 cm). More preferably, the blade cover 22 of the mini safety scalpel 20 may have a length between 5 and 9 cm (the length of the handle 24 may be between 2 and 4 cm and the length of the shaft 26 may be between 2 and 4 cm). Most preferably, the length of the blade cover 22 of the mini safety scalpel 20 may be approximately 7 cm (the length of the handle 24 may be approximately 3.2 cm and the length of the shaft 26 may be approximately 3.8 cm). The length of the mini scalpel 20 may increase when the blade body 60 is extended and exposed in the use position 54. The length of the mini scalpel 20 in the use position 54 may depend on the length of the blade 61, the length of the blade carrier 62, and the amount that the blade body 60 is extended from the housing 23.

Mini Safety Scalpel 20 Positions

As shown in FIGS. 2A-2D, 3A-3D, and 4A-4F, a blade body 60 is movable (extendable and retractable) and lockable within the blade cover 22. As the pusher 40 is moved along at least a portion of the length of the blade cover 22, the blade body 60 may also be moved between the use position 54, the stowed position 52, and the safety position 50. The position and amount of movement of the blade body 60 may be directly related to that of the pusher 40. As described further herein, the blade body 60 locks with the front lock member 44, the back lock member 45 and the safety lock member 70 to prevent the blade body 60 from inadvertently being moved out of one of the three different locked positions.

Figure 2A:
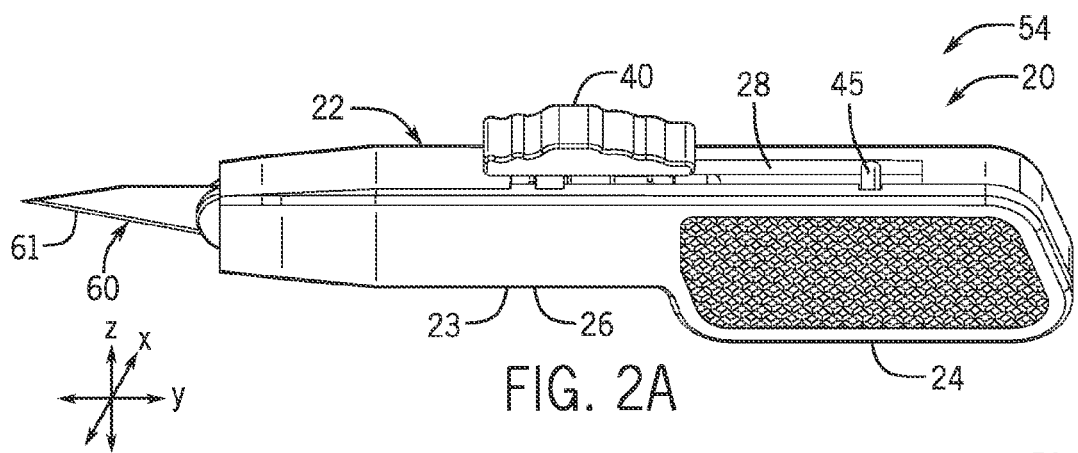
FIGS. 2A-2D are perspective views of the mini scalpel of FIG. 1A moving from a stowed position, to an unlocked position, to a stowed position, and to a safety position.
Figure 3A:
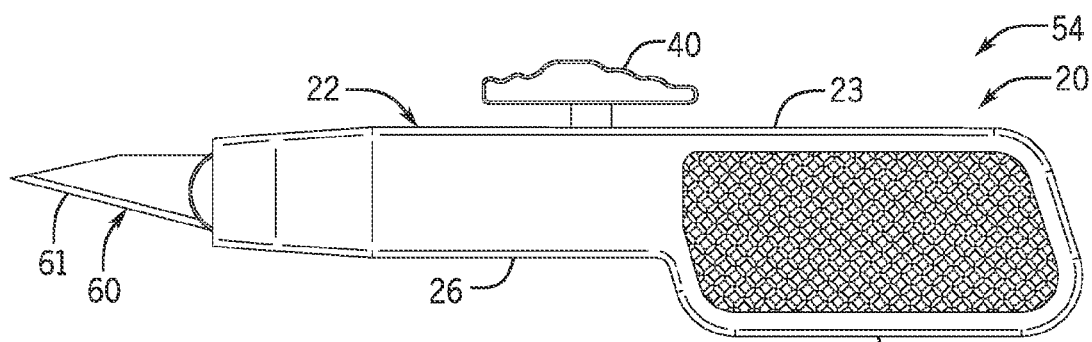
FIGS. 3A-3D are front views of the mini scalpel of FIG. 1A moving from a stowed position, to an unlocked position, to a stowed position, and to a safety position.

As shown in FIGS. 2A, 3A, and 4A, the blade body 60 may be positioned and locked in first locked position or an extended, exposed, or use position 54. In the use position 54, the blade body 60 may be at least substantially extended along the length of the blade cover 22 (e.g. from the end of the shaft 26), such that the blade 61 is exposed outside of the housing 23 and the scalpel 20 may effectively be used as a cutting instrument. The blade body 60 may be locked into the use position 54 (as described further herein) to keep the blade 61 steady and stationary relative to the blade cover 22 and to provide tension to allow the user to effectively use the blade 61. Therefore, in the use position 54, the blade 61 will not retract while the scalpel is being used. In the use position 54, a first hook 42 of the pusher 40 may be locked with a front lock member 44 of the blade cover 22.

Figure 2B:
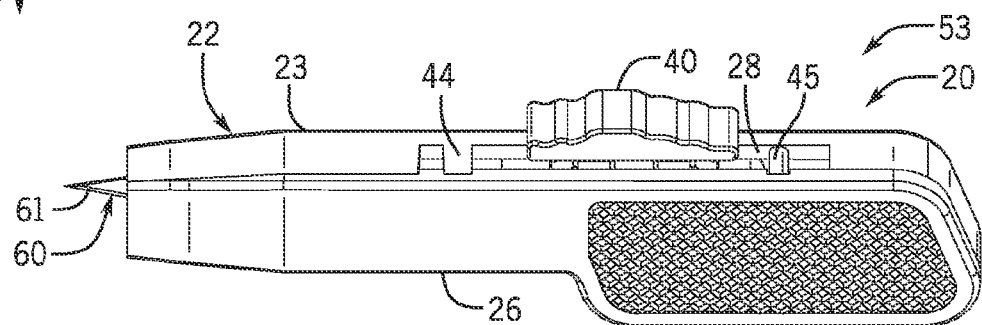
Figure 3B:
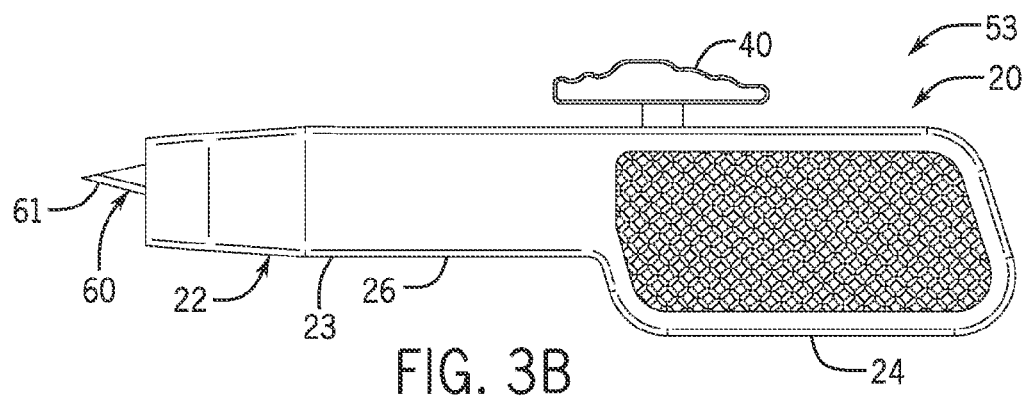

As shown in FIGS. 2B, 3B, and 4C, the blade body 60 may be in an unlocked position 53 while the blade body 60 is being moved between the use position 54 and the stowed position 52. In the unlocked position 53, the blade body 60 is free to move along at least a portion of the length of the blade cover 22, thereby exposing different amounts of the blade 61 outside of the housing 23. The pusher 40 (and the blade body 60) may be easily moved by the user between the use position 54, the unlocked position 53, and the stowed position 52, as described further herein.

Figure 2C:
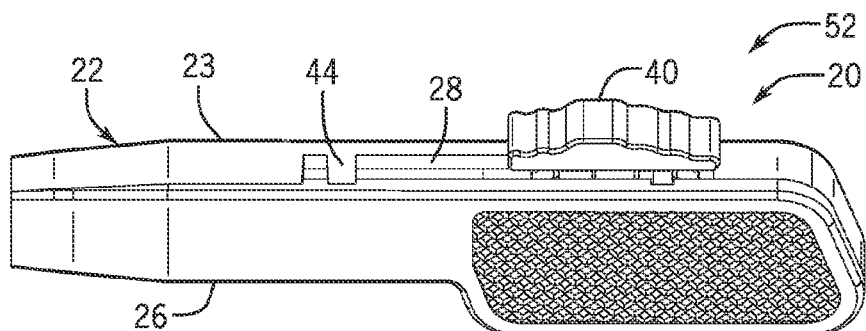
Figure 3C:
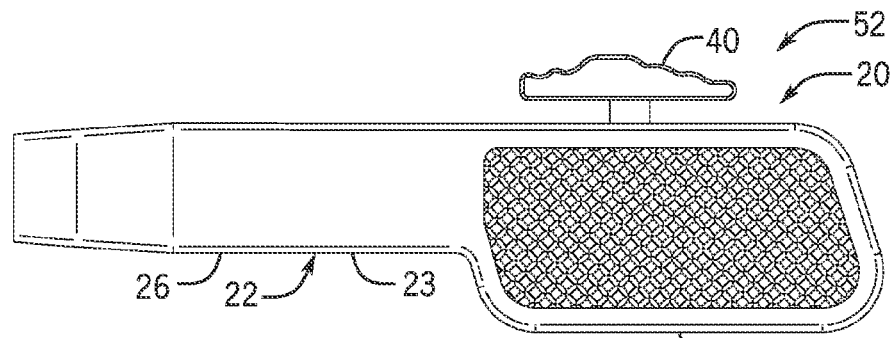

As shown in FIGS. 2C, 3C, and 4E, the blade body 60 may be positioned and locked in a second locked position or a retracted, storage, or stowed position 52. In the stowed position 52, the blade body 60 may be retracted and the blade 61 fully concealed within the housing 23, such that there are no sharp portions of the blade 61 outside of the housing 23. As shown in FIG. 4E, the blade 61 may be located at least partially within the shaft 26 of the housing 23 in the stowed position 52. However, it is anticipated that the blade body 60 may be stored at least partially within any portion of the housing 23, such as the handle 24. The blade body 60 may be locked into the stowed position 52, preventing the blade 61 from inadvertently being moved into an exposed position. Since the blade 61 is completely within the housing 23, the blade 61 does not pose any risk toward any nearby people or objects if, for example, the scalpel 20 is dropped or mishandled. In the stowed position 52, a second hook 43 of the pusher 40 may be locked with a back lock member 45 of the blade cover 22.

Figure 2D:
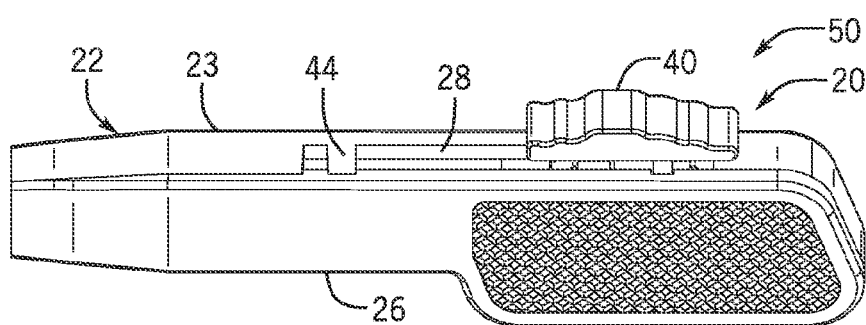
Figure 3D:
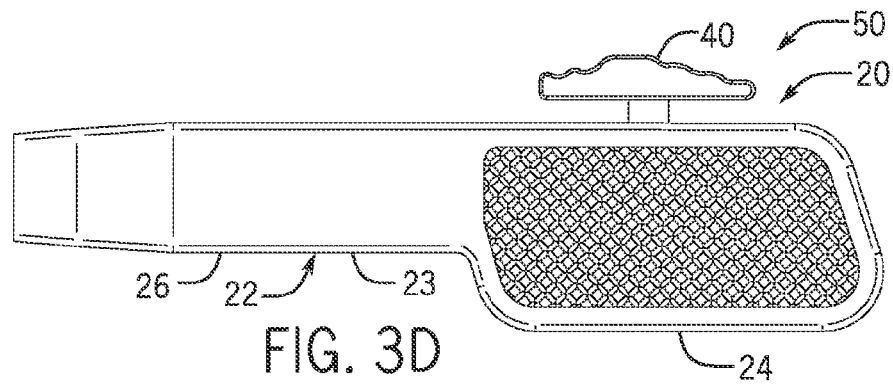

As shown in FIGS. 2D, 3D, and 4F, the blade body 60 may be positioned and locked in a third locked position or a safety position 50. In the safety position 50, the blade body 60 may be fully retracted and the blade 61 fully concealed within the housing. The blade body 60 may be retracted further into the housing 23 in the safety position 50 than the stowed position 52. In the safety position 50, the blade body 60 is strongly secured or locked within the blade cover 22, requiring a purposeful or strong force to actuate the scalpel 20 to disengage the lock mechanism out of the safety position 50. The force required to move the blade body 60 out of the safety position 50 is greater than the force required to move the blade body 60 out of the use position 54 and the stowed position 52. Once the user is finished using the scalpel 20, the user may move the blade body 60 into the housing 23, past the stowed position 52, and into the safety position 50. Thus, the safety position 50 may act as a final locking position and may be used once the scalpel 20 is no longer needed (e.g. when it is thrown away) to securely hold the blade body 60 within the housing 23 and prevent the blade body 60 from inadvertently being exposed. It is further anticipated that the scalpel 20 may be shipped and/or placed on the surgical tray in the safety position 50 (however, according to another embodiment, the scalpel 20 may be in the stowed position 52 (ready to be used) during shipment and/or on the surgical tray). In the safety position 50, a safety hook 68 of the blade body 60 may be locked with a safety lock member 70 of the blade cover 22.

In order to move the blade body 60 between the use position 54, the stowed position 52, and the safety position 50, the pusher 40 may slide at least partially along the length of the housing 23 (along a slot 28 of the housing 23, as shown in FIGS. 2A-2D and along the longitudinal axis (i.e., the y-axis of the scalpel 20)) to push or pull the blade body 60 out of or back into the housing 23. As the pusher 40 is slide back and forth, the blade body 60 may directly follow the movement of the pusher 40 into the three locked positions. For example, the pusher 40 may be located closer to the end of the handle 24 (away from the shaft 26) in the safety position 50 and closer to the end of the shaft 26 (away from the handle 24) in the use position 54. In the stowed position 52, the pusher 40 may be located between the respective positions of the safety position 50 and the use position 54.

In order to lock the blade body 60 (and, thereby, the blade 61) to the blade cover 22 in the use position 54 and the stowed position 52, the pusher 40 may cooperate with the front lock member 44 and the back lock member 45, respectively. More specifically, as shown in FIG. 4A, a first lip or hook 42 of the pusher 40 may hook or wrap at least partially over or around the front lock member 44 in the use position 54. The front lock member 44 is sandwiched between the first hook 42 and a middle stem 46 of the pusher 40 and the first hook 42 is locked between the front lock member 44 and the body of the blade cover 22, thereby preventing the pusher 40 (and, thereby, the blade body 60) from moving in either direction. Similarly, as shown in FIG. 4E, the second lip or hook 43 of the pusher 40 may hook or wrap at least partially over or around the back lock member 45 in the stowed position 52. The back lock member 45 is sandwiched between the second hook 43 and a middle stem 46 of the pusher 40 and the second hook 43 is locked between the back lock member 45 and the body of the blade cover 22, thereby preventing the pusher 40 from moving in either direction. The user may optionally move the scalpel 20 between the use position 54 and the stowed position 52 multiple times for multiple uses.

It is anticipated that the pusher 40 may optionally be locked anywhere along the length of the blade cover 22 (and within the slot 28). For example, the blade cover 22 may include additional lock members along the length of the blade cover 22 to secure or lock with at least one of the hooks 42 or 43, thereby locking the pusher 40 and the blade body 60 to the blade cover 22.

In order to move the pusher 40 between the unlocked position 53 and either the use position 54 or the stowed position 52 (e.g., to lock and unlock the pusher 40 and the blade body 60), one side of the pusher 40 may be compressed or pushed down into the blade cover 22, as shown in FIGS. 4B and 4D. By pushing down one side of the pusher 40 or pivoting the pusher 40, the first hook 42 and/or the second hook 43 of the pusher 40 may be forced downward (further into the blade cover 22), allowing one of the first hook 42 or the second hook 43 to move around or beneath either the front lock member 44 or the back lock member 45 (as shown in FIGS. 4B and 4D). As the pusher 40 is released, the pusher 40 may automatically move back upward (at least partially out of the blade cover 22) due to a spring 48 (as described further herein).

In order to move into and lock the blade body 60 in the safety position 50, the pusher 40 may be moved from the use position 54 to the stowed position 52 and past the stowed position 52 along the longitudinal length of the blade cover 22, such that at least one safety hook 68 along one end of the blade body 60 engages and locks with the safety lock member 70 within the blade body 60.

For example, in order to move the blade body 60 from the use position 54 (as shown in FIGS. 2A, 3A, and 4A) to the stowed position 52 (as shown in FIGS. 2C, 3C, and 4E), the pusher 40 may first be unlocked by pushing, rotating, or pivoting the trailing side (e.g., the left side in this example) of the pusher 40 downward while sliding the pusher 40 to the right (as shown in FIG. 4B) to move the first hook 42 past and beneath the front lock member 44 and to free the first hook 42 from the front lock member 44. As shown in FIGS. 2B, 3B, and 4C, the pusher 40 and the blade body are now in the unlocked position 53 and may freely move or slide in either direction along the slot 28 between the front and back lock members 44 and 45. As the pusher 40 is moved to the right, the blade 61 may retract into the housing 23.

Once the pusher 40 reaches the back lock member 45 of the blade cover 22, the leading side (e.g., the right side in this example) of the pusher 40 may be pushed or rotated or pivoted downward as the pusher 40 continues to move or slide to the right (as shown in FIG. 4D), allowing the second hook 43 to move beneath and past the back lock member 45. As the pusher 40 is released, the rightmost side of the pusher 40 moves upward, securing the second hook 43 between the body of the blade cover 22 and the back lock member 45, thereby locking the pusher 40 and the blade body 60 into the stowed position 52, as shown in FIGS. 2C, 3C, and 4E. The pusher 40 is forced further along the slot 28, thereby moving the blade body 60 further along the housing 23 and snapping the safety hook 68 and the safety lock member 70 together. Conversely, in order to move the blade body 60 from the safety position 50 to the stowed position 52 and then to the use position 54, the opposite procedure may be followed.

The Blade Cover 22 of the Mini Safety Scalpel 20

Figure 6A:
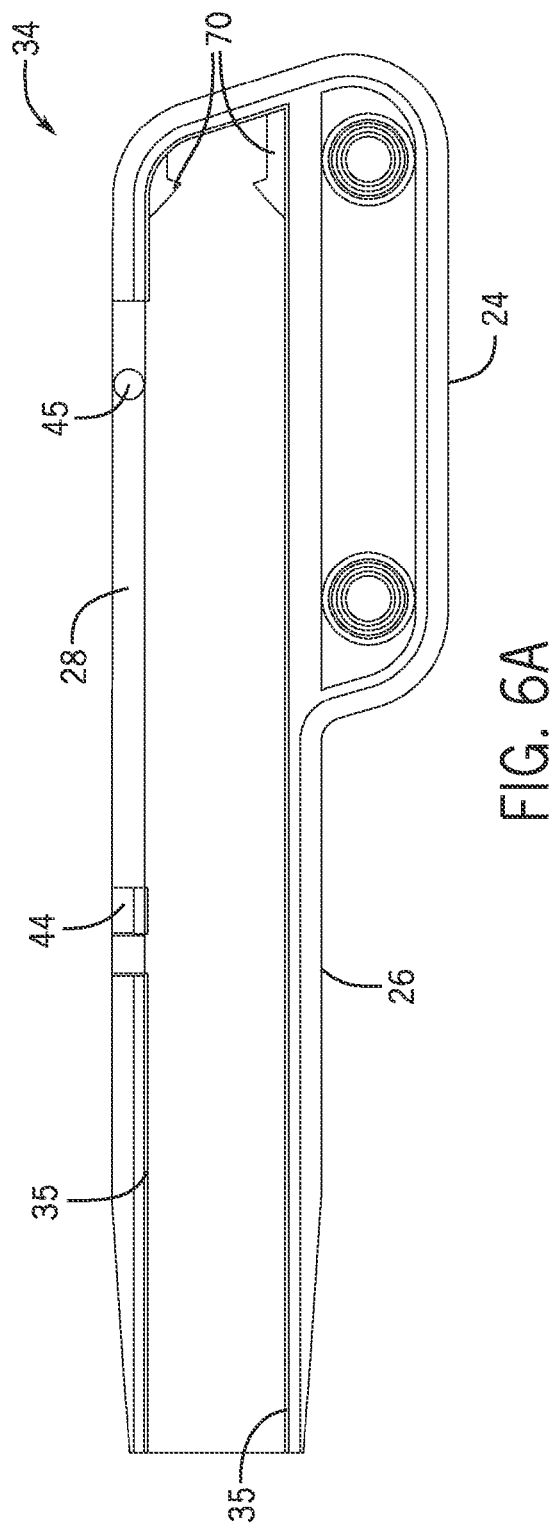
FIGS. 6A-6B are inside, front and perspective views, respectively, of a back side of the mini scalpel of FIG. 1A.
Figure 6B:
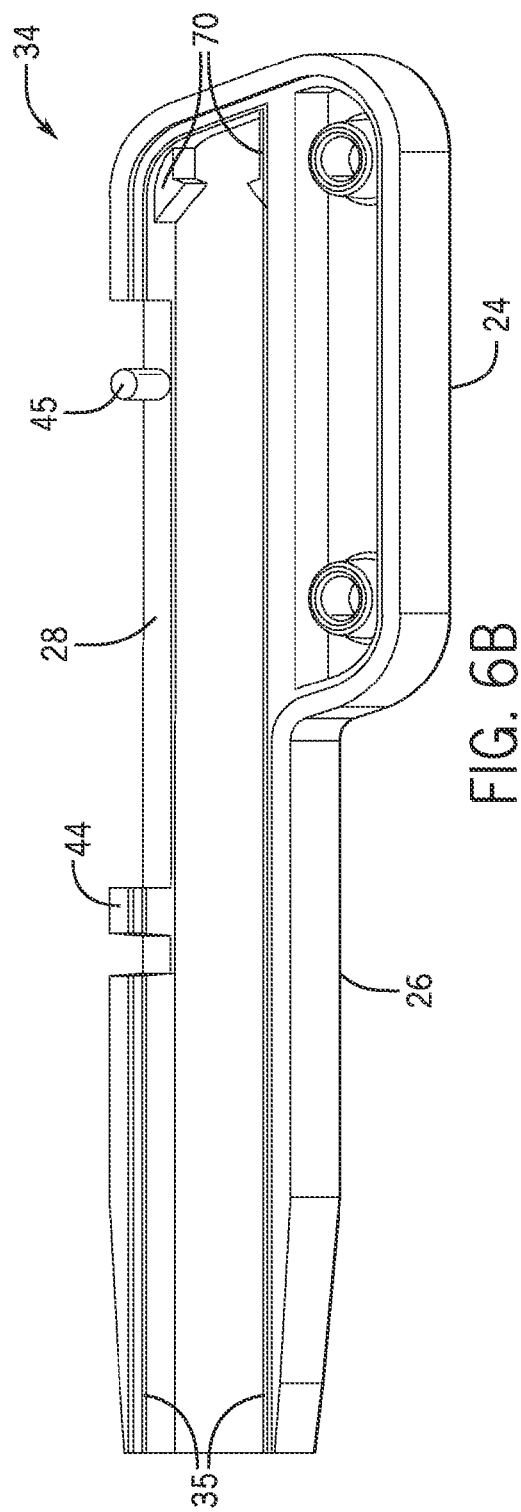

The blade cover 22 may include a front lock member 44, a back lock member 45, and a safety lock member 70. The front lock member 44, the back lock member 45, and the safety lock member 70 may be located on the front side 32 and/or the back side 34 of the blade cover 22 and may be shaped according to the desired configuration including, but not limited to, notches, tabs, lips, hooks, or snaps. The lock members 44, 45, and 70 may be shaped to complement and lock with (e.g., snap, clip, or secure with) the first hook 42, the second hook 43, and the safety hook 68, respectively. According to one embodiment as shown in FIGS. 6A-6B, the front lock member 44 is a substantially rectangular and larger tab, while the back lock member 45 is a substantially round and smaller tab. The safety lock member 70 may include a variety of different mechanisms including clips, attachments, claws (such as retention tabs), snaps, or hooks that are complementary to the safety hook 68 on the blade body 60. As shown in FIG. 6F, the safety lock member 70 may include two hooks to lock with two safety hooks 68 on the blade body 60 in order to provide a stronger locking mechanism in the safety position 50.

The lock members 44, 45, and 70 may be located within a variety of different areas within the blade cover 22. According to one embodiment, the lock members 44 and 45 may be located along the slot 28 between the front side 32 and the back side 34 of the blade cover 22 in order to correspond with the hooks 42 and 43 of the pusher 40. The lock members 44 and 45 may optionally be located toward opposite ends of the slot 28. The slot 28 may optionally include additional lock members along the length of the slot 28 to allow the pusher 40 to be secured or locked into any position along the slot 28, exposing different amounts of the blade 61 according to the desired configuration. According to one embodiment, the safety lock member 70 may be located on a distal end of the blade cover 22 (e.g., opposite to the end where the blade 61 is exposed in the use position 54) such that the blade body 60 is fully retracted within the blade cover 22 in the safety position 50.

The blade cover 22 may also include a housing 23, a handle 24 and a shaft 26. The housing 23 may be used to contain or house the blade body 60 and conceal the blade 61 (in the stowed position 52 and the safety position 50. The handle 24 of the blade cover 22 may provide an area for the user to securely hold onto and manipulate the scalpel 20 with either hand. For example, the handle 24 may comprise a relatively wider area than the shaft 26 to provide more surface area for the user to hold. The handle 24 may include contours to allow the user to ergonomically hold and grip the scalpel 20. For example, the handle 24 may include a front lip for a finger of the user to at least partially wrap around, while the thumb may rest on a top portion of the blade cover 22 to move the pusher 40. The front lip may extend beyond the shaft 26 in any direction, such that the handle 24 has a greater thickness than the shaft 26 for the user to hold. For example, the front lip may extend beyond the shaft 26 in the vertical direction (with respect to FIG. 6A).

The shaft 26 may be a relatively narrower or smaller portion of the scalpel 20 extending out from the handle 24 to allow the scalpel 20 to access smaller surgical areas. The blade 61 may extend out of the blade cover 22 through the shaft 26 (e.g., away from the handle 24). The blade body 60 may be movable within both the handle 24 and the shaft 26.

The blade cover 22 may be sized to fit within the hand of a user, such as a surgeon. The overall size of the blade cover 22 may be smaller (length (the longitudinal or y-axis), width (the x-axis), and/or height (the z-axis)) than that of a regular, long-handled scalpel. Although the handle 24 and the shaft 26 of the blade cover 22 are each shown in a substantially rectangular configurations (along the y-z plane as shown, for example, in FIG. 1A) and the end of the shaft 26 is shown as rectangular (see, e.g., FIG. 1C), it is anticipated that the various components of the blade cover 22 may be shaped according to a desired configuration such as, for example, an oval, ellipse, or circle.

As shown in FIGS. 6A-6H and 7A-7G, the blade cover 22 of the scalpel 20 may include two faces or sides (a back side 34 and a front side 32), detachable along the length of the blade cover 22. The back side 34 and the front side 32 of the blade cover 22 may complement each other such that the pusher 40 and the blade body 60 are properly secured, while guiding the movement of the blade body 60 between the use position 54, the stowed position 52, and the safety position. However, it is anticipated that the front side 32 and the back side 34 may be shaped according to the desired configuration. For example, the front side 32 and the back side 34 may cover a different number of sides of the blade body 60 or may be shaped differently from the embodiments shown in the figures.

Figure 5:
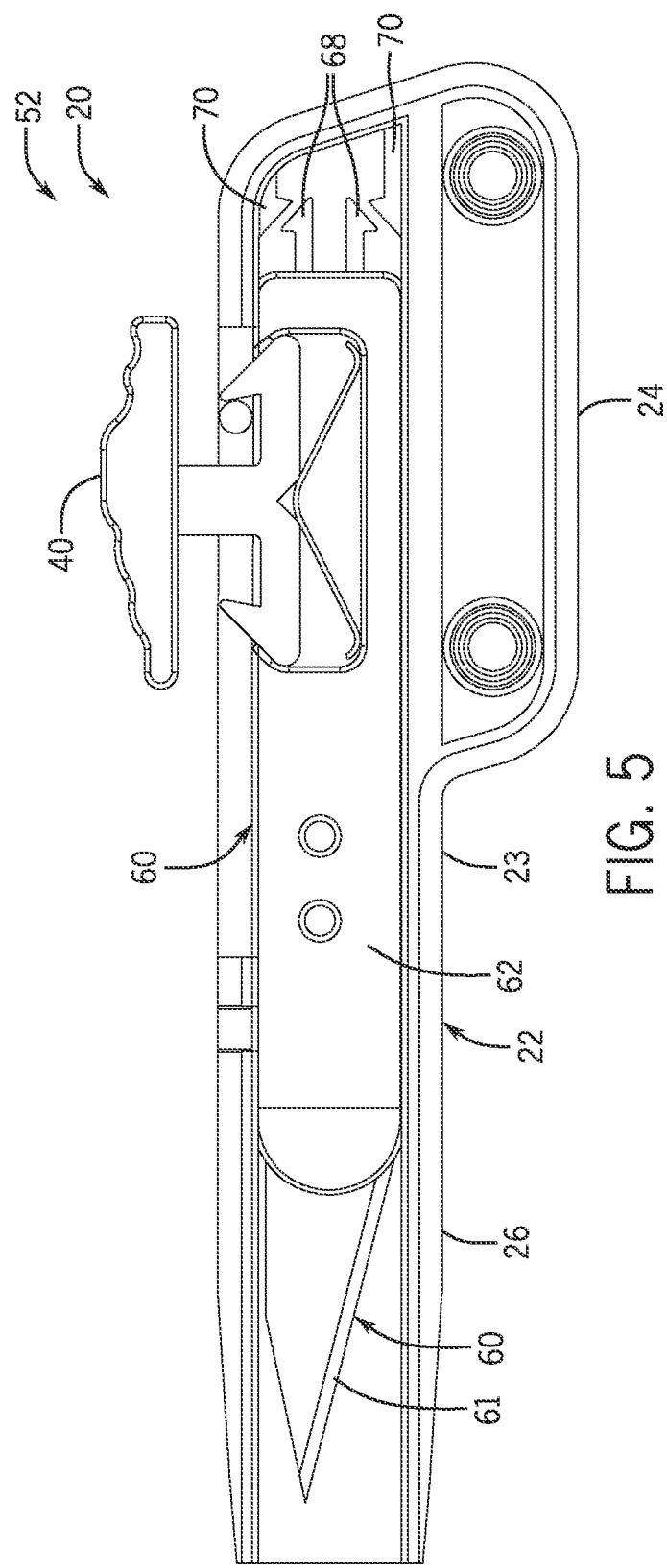
FIG. 5 is a cut away, front view of the mini scalpel of FIG. 1A in a stowed position.

According to one embodiment, the back side 34 of the blade cover 22, as shown in FIGS. 6A-6H, may house or hold the various movable components of the scalpel 20. For example, the pusher 40 may move along the slot 28 that is at least partially within the back side 34. The back side 34 may be shaped to complement the shape of the blade body 60 and may substantially cover multiple sides of the blade body 60, such that the blade body 60 is secured and guided within the shaft 26 and the handle 24, which prevents the blade 61 from unnecessarily moving or wobbling. As shown in FIG. 5, the back side 34 covers four sides (e.g., the top, bottom, one side, and back) of the blade body 60 and allows the blade body 60 to move longitudinally along the y-axis. Further, as shown in FIGS. 6B and 6F, the back side 34 (and/or the front side 32) may include longitudinal or lengthwise lips, edge, or bumps 35 along the length of the shaft 26 to guide, hold, and secure the blade body 60 and the pusher 40 within the housing 23 and prevent the blade body 60 from moving side to side (e.g., along the x-axis).

The front side 32 of the blade cover 22, as shown in FIGS. 7A-7G, may at least partially cover at least one side of the back side 34, such that the blade body 60 is substantially enclosed and the pusher 40 is at least partially exposed outside of the blade cover 22. The front side 32 may secure the blade body 60 and the pusher 40 within the blade cover 22 such that the pusher 40 may move along the slot 28 to move the blade 61 at least partially outside of the blade cover 22 into the use position 54.

The back side 34 and the front side 32 may include mechanisms to allow for temporary or permanent attachment to each other. For example, the back side 34 and the front side 32 may include complementary snaps and/or notches, as well as utilize glue and/or ultrasonic welding, to attach with each other. The attachments may be located anywhere within the blade cover 22, such that the pusher 40 and the blade body 60 are able to slide or move properly. As shown in FIGS. 6A, 6B, 6E, 7A, 7C, and 7D, the attachment sites may be within the handle 24. Alternatively or additionally, the front side 32 and the back side 34 may be attached along or within at least a portion of the perimeter of the blade cover 22. If the attachments are temporary, the front side 32 may be removed from the back side 34 and at least the blade body 60 may be replaced for maintenance, repair, replacement, cleaning, or disinfecting.

The slot 28 between the front side 32 and the back side 34 may provide an area for the middle stem 46 of the pusher 40 to move along a length of the blade cover 22, allowing a top half of the pusher 40 (which the user may directly contact to move the pusher 40) to be exposed outside of the housing 23, while a bottom half (which may include the first and second hooks 42 and 43) may move within the housing 23. The width of the slot 28 may smaller than the width of the bottom half of the pusher 40, such that the pusher 40 is secured along the x- and y-axes within the housing 23, even if in the unlocked position 53.

The Movable Components of the Mini Safety Scalpel 20

Figure 8A:
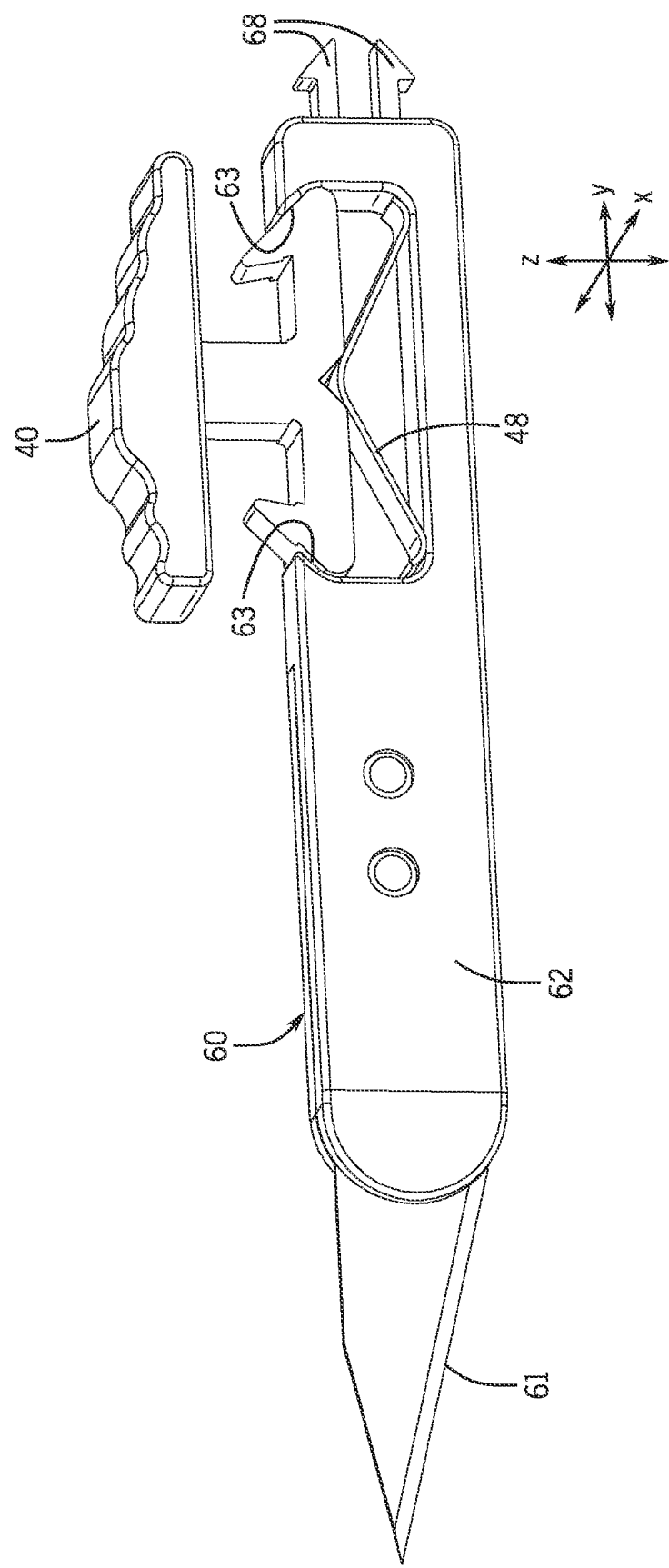
FIG. 8A is a front view of a blade body, a spring, and a pusher used within the scalpel of FIG. 1A.
Figure 8B:
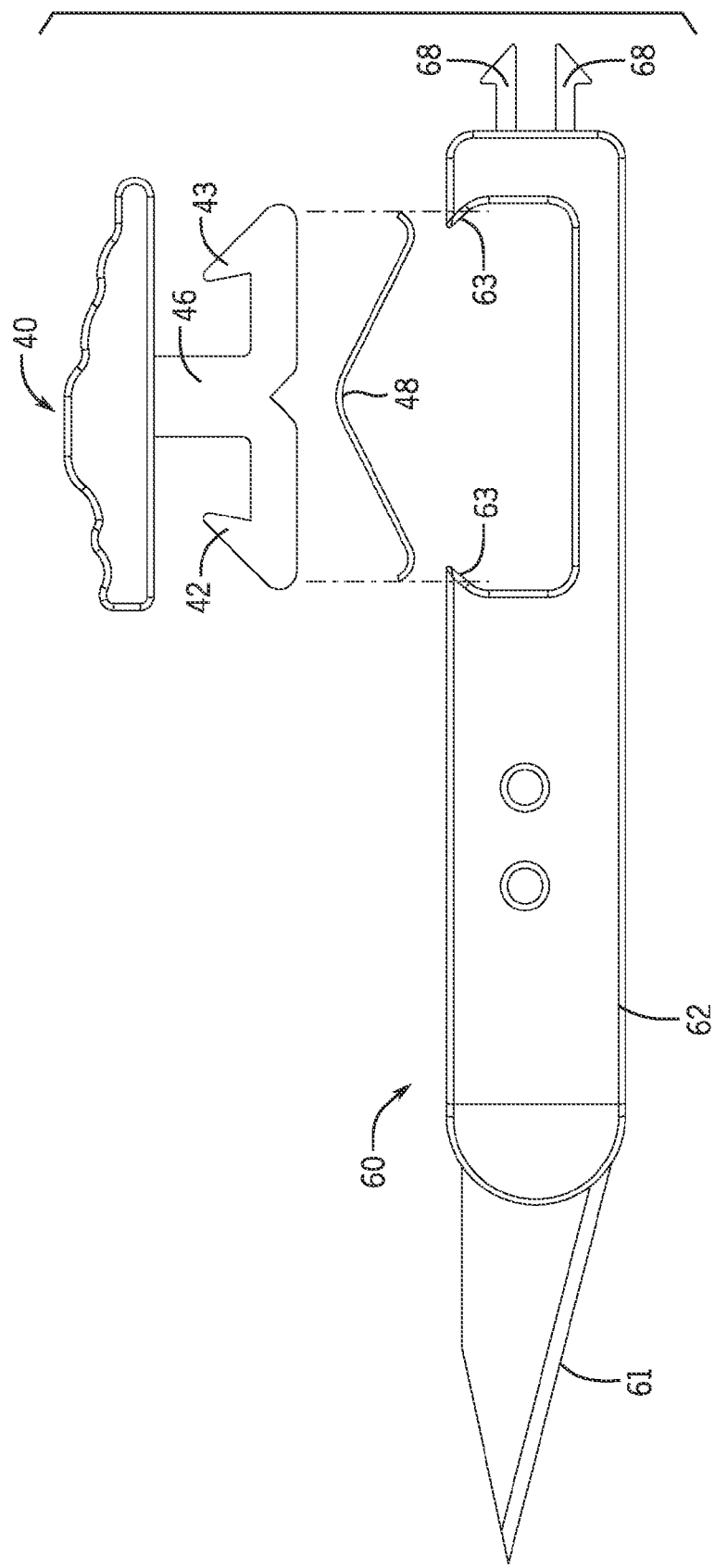
FIG. 8B is an exploded, front view of the blade body, the spring, and the pusher used within the scalpel of FIG. 1A.
Figure 10A:
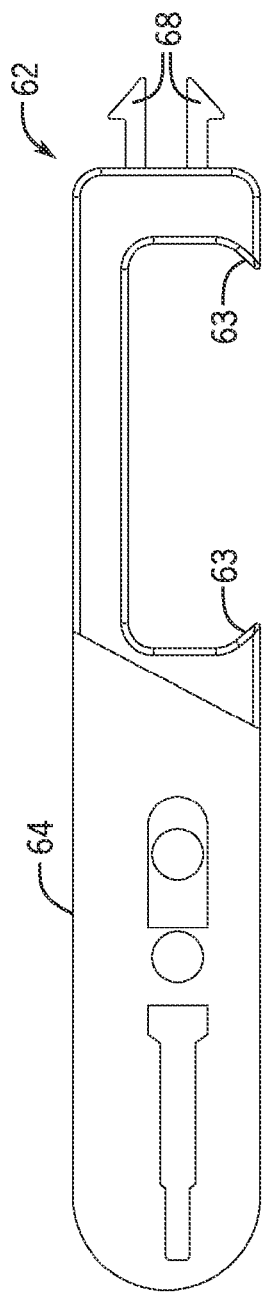
FIG. 10A is a back view of a blade carrier body that can be used within the scalpel of FIG. 1A.
Figure 10B:
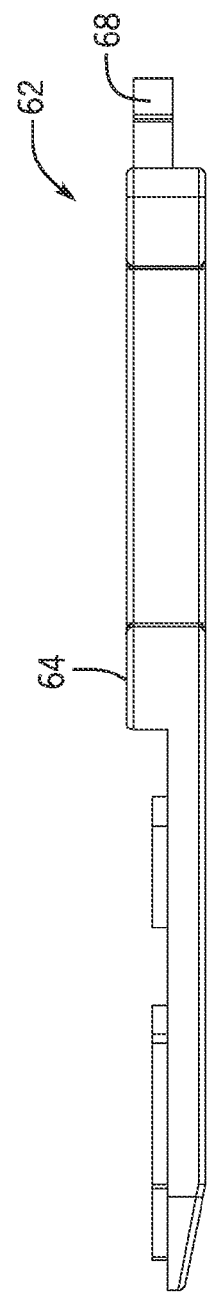
FIG. 10B is a top view of the blade carrier body of FIG. 10A.
Figure 10C:
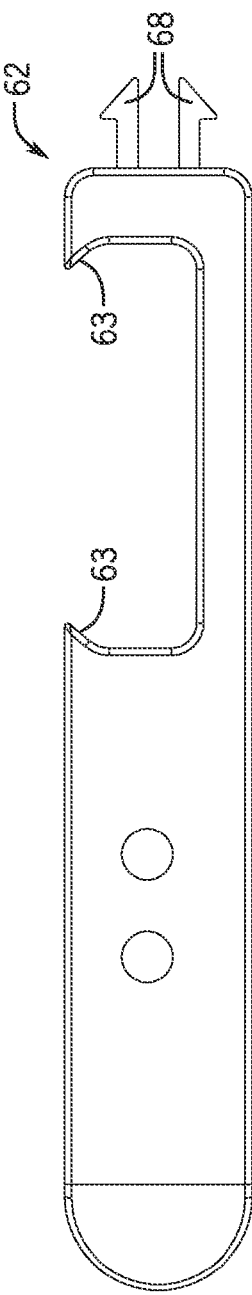
FIG. 10C is a front view of the blade carrier body of FIG. 10A.
Figure 10D:
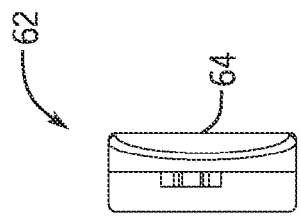
FIG. 10D is a left side view of the blade carrier body of FIG. 10A.
Figure 12:
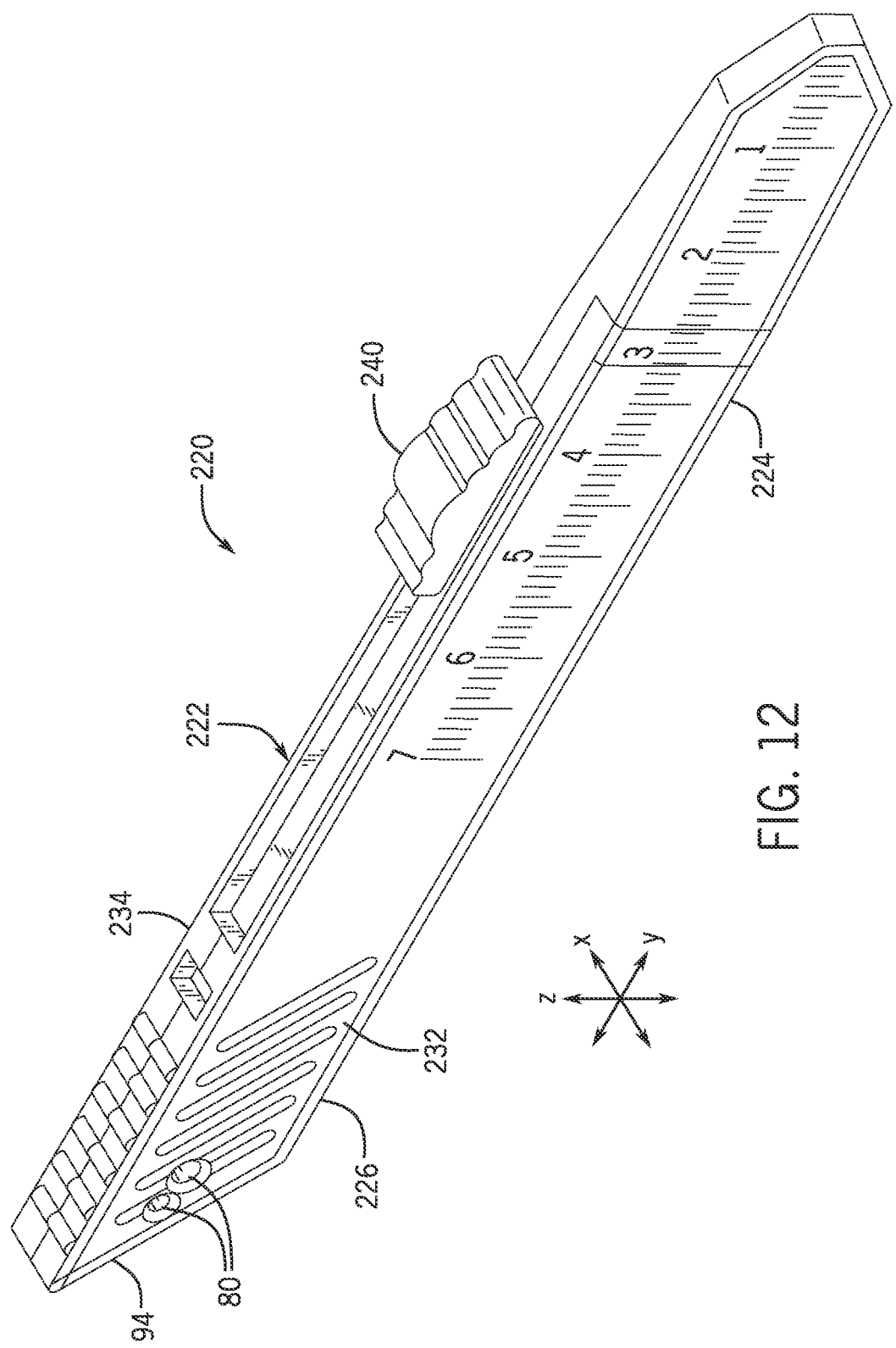
FIG. 12 is a perspective view of a long-handled scalpel according to one embodiment.
Figure 14A:
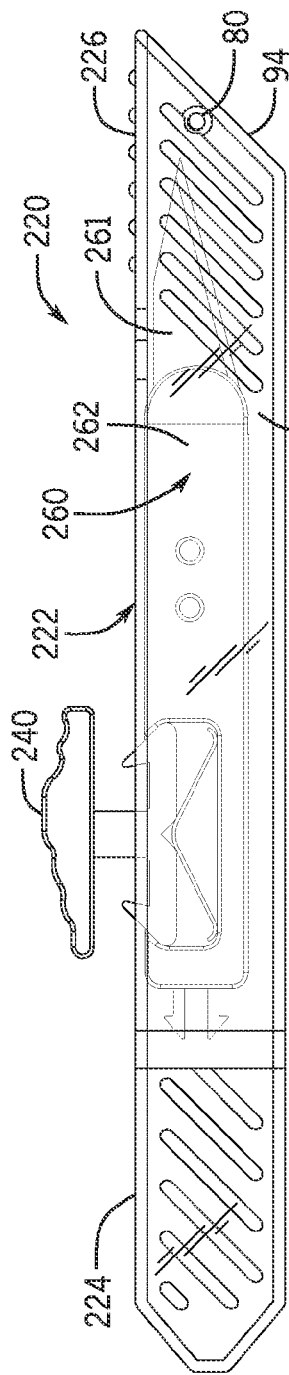
FIGS. 14A-14B are front and top views, respectively, of a long-handled scalpel according to yet another embodiment.
Figure 14B:
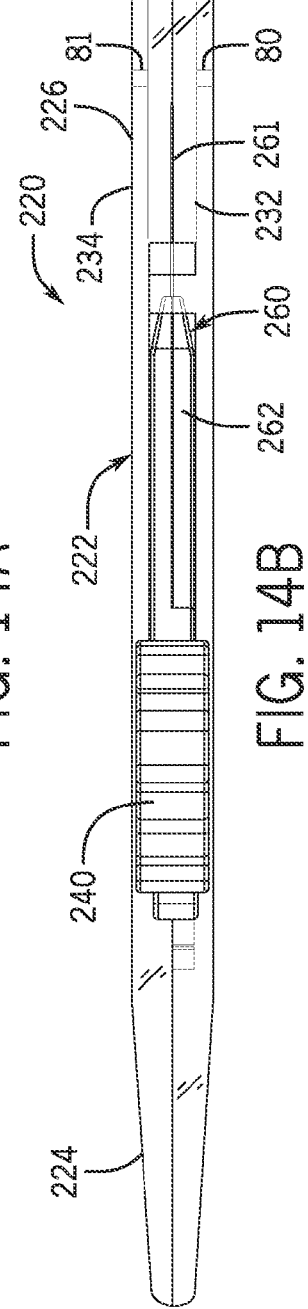
Figure 15:
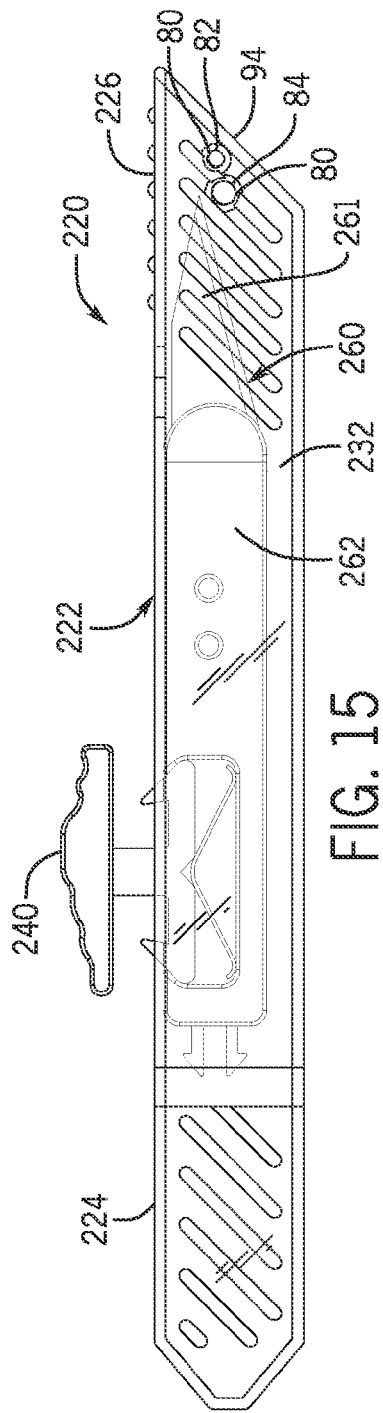
FIG. 15 is a front view of a long-handled scalpel according to another embodiment.

FIGS. 8A-8B depict movable components that are movable and lockable relative to the blade cover 22. The movable components may include the blade body 60, the pusher 40, and a spring 48. As the pusher 40 is moved along the blade cover 22, these movable components may move congruently at least partially within the housing 23. For example, as the pusher 40 is moved, the pusher 40 may directly or indirectly cause the blade body 60 and the spring 48 to move within the housing 23. Likewise, when the pusher 40 is locked to the blade cover 22, the blade body 60 and the spring 48 are also locked in place with the pusher 40.

The pusher 40 may extend from outside of the housing 23 into the housing 23 to allow the user to control, as well as lock, the position of the blade body 60 with respect to the blade cover 22. For example, the pusher 40 may be moved forward along the length of the blade cover 22 (e.g., away from the handle 24) to extend the blade 61 out of the shaft 26. Conversely, the pusher 40 may be moved backward along the length of the blade cover 22 (e.g., toward the handle 24) to retract the blade 61 into the shaft 26. The pusher 40 may also be used to lock the blade body 60 into any position along the length of the blade cover 22, as described further herein.

The pusher 40 may include a variety of mechanisms to lock or attach with the front and back lock members 44 and 45. For example, as shown in FIGS. 8B and 9A, the pusher 40 may include a first hook 42 and a second hook 43 on either side of the pusher 40. The first hook 42 is configured to engage with the front lock member 44 to lock the blade body 60 to the blade cover 22 in the use position 54. The second hook 43 is configured to engage the back lock member 45 to lock the blade body 60 to the blade cover in the stowed position 52. To lock the pusher 40 (and the blade body 60) in place, the front and back lock members 44 and 45 may be secured between the innermost side of the respective hook 42 or 43 and the middle stem 46 of the pusher 40.

The outermost edge or side of the hooks 42 and 43 may be sloped or angled to allow the hooks 42 and 43 to be easily moved around the lock members 44 or 45 into the use or stowed position 54 or 52. The topmost portion of the hooks 42 and 43 may include a relatively small tip to minimize the amount of area the hooks 42 and 43 must move beneath the lock members 44 and 45. The tip may be at a sharp angle or may have a relatively short length. The innermost edge or side of the hooks 42 and 43 may be, for example, substantially upright or at 90° relative to the horizontal axis of the hooks 42 and 43 in FIGS. 8B and 9A in order to help the hooks 42 and 43 snap or move around the lock members 44 and 45 into a locked position, as well as maintain a lock with the lock members 44 and 45.

According to another embodiment, the pusher 40 may include a stair-step configuration to mate with a stair-step configuration on the slot 28 of the blade cover 22 to allow the user to lock the pusher 40 into any position along the slot 28 and customize the exact amount of exposed blade 61.

As shown in FIGS. 8B and 9A, the pusher 40 may be ergonomically contoured and shaped to be pushed and retracted by a finger (e.g. a thumb) of the user, while the user is holding the scalpel 20 in the same hand. The pusher 40 may be symmetrical or shaped to optimally fit both pushing and pulling motions of the thumb. For example, either side of the pusher 40 may have a different slope, shape, contour, and length according to the desired configuration. As shown in FIGS. 8A-8B and 9A-9C, the pusher 40 may have different contours or shape according to the desired configuration. As shown in a comparison of FIGS. 4E and 5, the pusher 40 may be oriented in either direction with respect to the blade cover 22.

The pusher 40 and the corresponding slot 28 may be located along any side of the blade cover 22 in order to be conveniently located for the user. According to one embodiment, the pusher 40 may be movable along the top of the blade cover 22, as shown in FIGS. 2A-2D. As the user holds the scalpel 20 in one hand, the user may use his or her thumb of the same hand to press and move the pusher 40. The user may hold and operate the scalpel 20 in either hand.

According to one embodiment, feedback may be provided to the user to ensure the user that the pusher 40 has been properly locked or unlocked. For example, the hooks 42 and 43 and the lock members 44 and 45 may interact such that as the pusher 40 is locked or unlocked, an audible snap or click may be heard. Alternatively or additionally, locking or unlocking the pusher 40 may result in a tactile sensation to confirm that the pusher 40 is locked or unlocked.

A spring 48 may be used to bias the pusher 40 to automatically spring or move upward relative to and away from the longitudinal centerline of the blade body 60 and vertically toward the front lock member 44 or the back lock member 45. Therefore, for example, depending on the relative positioning of the pusher 40 relative to the front and back lock members 44 and 45 and due to the spring 48, the pusher 40 may automatically move into a locked position (e.g., the use position 54 or the stowed position 52) in the absence of an outside force or pressure. The spring 48 may allow the pusher 40 to be vertically movable with respect to the blade cover 22, thus allowing the first hook 42 to be engaged or disengaged from the front lock member 44 and the second hook 43 to be engaged or disengaged from the back lock member 45 by pushing the pusher 40 into the housing 23 (e.g., toward the longitudinal centerline of the blade body 60), which compresses the spring 48.

As shown in FIGS. 8A and 8B, the spring 48 may be positioned between the pusher 40 and the blade body 60. The middle of the spring 48 may push up against the middle of the pusher 40. When the pusher 40 is pressed into the blade cover 22 (as shown, for example, in FIGS. 4B and 4D), the spring 48 may be at least partially compressed within the housing 23 to allow the pusher 40 to move further into the housing 23 and to move one of the hooks 42 or 43 beneath or around the respective lock member 44 or 45 to lock or unlock the pusher 40. By using one point of contact between the middle of the spring 48 and the middle of the pusher 40, the pusher 40 may pivot to either longitudinal side to lower one of the hooks 42 or 44 more easily within the blade cover 22 and move the respective front or back lock member 44 or 45.

The spring 48 may be a variety of different springs, including but not limited to coil or helical springs, leaf springs, balance springs, cantilever springs, or flat springs. Alternatively or additionally, other components may be used to bias the pusher 40 away from a longitudinal centerline of the blade body 60. According to another embodiment, the spring 48 may provide a sufficient spring force to firmly secure and lock the pusher 40 into any position along the slot 28.

The pusher 40 may be movably connected to the blade body 60, such that longitudinal movement (along the y-axis) of the pusher 40 moves the blade body 60 and the pusher 40 is movable along the z-axis relative to the blade body 60 to lock or unlock the pusher 40. The blade body 60 and the pusher 40 may be a single piece or separate components.

As shown in FIG. 8A, the pusher 40 may be surrounded on both longitudinal ends by the blade body 60 such that the pusher 40 may cause the blade body 60 to move in either direction along the length of the housing 23. Additionally, as shown in FIGS. 8A, 8B, 10A, and 10C, the blade body 60 may include sloped edges 63 to secure or hold the pusher 40 within the housing 23. The sloped edges 63 may be complementary to the outermost edges of the first and second hooks 42 and 43 in order to secure the pusher 40.

The blade body 60 may include a blade 61 and a blade carrier 62. As shown in FIGS. 8A-8B, 10A-10D, and 11A-11D, the blade carrier 62 may be designed to securely and statically hold and move with the blade 61 within the housing 23, as well as to lock the blade body 60 into the safety position 50. The blade carrier 62 may include a variety of different attachment mechanisms including, but not limited to, at least one clip, attachment, lip, claw (such as a retention tab), snap, or safety hook 68 along the a portion of the blade carrier 62 to attach with the safety lock member 70 within the blade cover 22.

According to one embodiment as shown in FIGS. 6A-6B, 6E, 8A-8B, and 10A-10C, the blade carrier 62 may include safety hooks 68 to lock the blade body 60 in the safety position 60. The safety hooks 68 may be located at the end of the blade carrier 62 that is opposite the blade 61 and the safety lock member 70 may be located toward the end of the blade cover 22. When the blade body 60 is moved as far as possible into the housing 23, the safety hooks 68 are configured to corporate, attach, or engage with the safety lock member 70 on the inside end of the blade cover 22, thus locking the blade body 60 to the blade cover 22 in the safety position 50, as shown in FIG. 4F.

In order to secure the blade 61, the blade carrier 62 may include multiple different attachable components. For example, as shown in FIGS. 10A-10D and 11A-11D, the blade carrier 62 may include a blade carrier body 64 and a blade carrier backing 66. The blade carrier body 64 may be used to slide within the housing 23 and interact with the pusher 40. The blade carrier backing 66 may be used to secure the blade 61 to the blade carrier body 64, such that at least a portion of the blade 61 is sandwiched between the blade carrier backing 66 and the blade carrier body 64 and a portion of the blade 61 is exposed beyond the blade carrier 62. The blade carrier backing 66 and the blade carrier body 64 may be temporarily or permanently secured, according to the desired configuration. For example, the blade carrier 62 may temporarily or releasably secure the blade 61 to allow the blade 61 may be removed and/or replaced.

The blade carrier body 64 and the blade carrier backing 66 may complementarily fit together and may be substantially the same shape or may different shapes, as shown in FIGS. 10A-10D and 11A-11D. The blade carrier backing 66 and the blade carrier body 64 may include complementary attachment points to permanently or temporarily attach to each other and to hold the blade 61. For example, as shown in FIG. 11B, the blade carrier backing 66 may include notches, which may attach through holes within the blade 61 and into holes within the blade carrier body 64, thereby securing the three components together. Alternatively or additionally, glue and/or ultrasonic welding may be used for attachment.

Additional Features of the Mini Safety Scalpel 20

The scalpel 20 may include additional features, such as a measuring tool or ruler along the length of the scalpel 20. The ruler may optionally be raised or lowered from the surface of the blade cover 22 of the scalpel in order to provide a tactile ruler.

The scalpel 20 and the various components may be made out of a variety of materials, according to the desired use. For example, the blade 61 may be made out of metal (such as stainless steel, a composite, an alloy, or aluminum), hard plastic, or ceramic. The spring 48 may be made out of flexible material, such as metal or plastic. The blade cover 22, the pusher 40, and the blade carrier 62 (and the various included components) may be made out of a variety of different materials, including but not limited to metal, plastic, alloys, composites, polymers, or wood.

The scalpel 20 may be designed to be disposable or reusable. For example, the components within the scalpel 20, such as the blade body 60, may be removed or replaced by opening up the scalpel 20 and removing the desired components. This may allow for the scalpel 20 (or the various components within the scalpel 20) to be disinfected or for routine maintenance of the scalpel 20, such as sharpening the blade 61.

The scalpel 20 may be held and used by either hand (right or left), according to the user's preference. Further, the scalpel 20 only requires one hand for complete activation and deactivation. For example, the scalpel 20 requires the user to only use one hand to unlock, move, and lock the blade into place from the stowed position 52 to the use position 54, allowing the user to begin using the scalpel 20. Conversely, the user may also only have to use one hand to unlock, move, and lock the blade 61 from the use position 54 back into the stowed position 52 and further into the safety position 50, as described further herein.

The mini safety scalpel 20 may be used in and for a variety of different fields, settings, and uses. For example, the scalpel 20 may be used to make incisions in surgical procedures, such as for cutting into organs like the skin. The scalpel 20 may also be used to cut or slice other instruments. For example, it may be desired to cut a catheter in order to adjust or shorten the overall length of the catheter. The scalpel 20 may be used outside of medical procedures as a cutting or sharp instrument. For example, the scalpel 20 may be used as a knife.

Scalpel Hole

According to another embodiment as shown in FIGS. 12-19, the mini scalpel 20 (as shown, for example, in FIGS. 18-19) or a long-handled scalpel 220 (as shown, for example, in FIGS. 12-17) may include at least one aperture or hole 80 or 81 within the blade cover 22 or 222 of the scalpel 20 or 220 to help facilitate cutting or trimming certain elements, objects, or structures 90, including but not limited to a line, wire, catheter, string, tube, or IV. The structure 90 may be inserted through the hole(s) 80 or 81 in order to secure and position the structure 90 to allow the structure 90 to be subsequently cut by the blade 61 or 261. Although the long-handled scalpel 220 is referred to in FIGS. 12-17C, it is anticipated that the various embodiments shown may be also used within the mini scalpel 20, as shown, for example, in FIGS. 18 and 19 with the first hole 80 and the small hole 82 and large hole 84, respectively. Additionally, the long-handled scalpel 220 may have the various embodiments and features of the mini scalpel 20 that are described further herein.

Figure 16A:
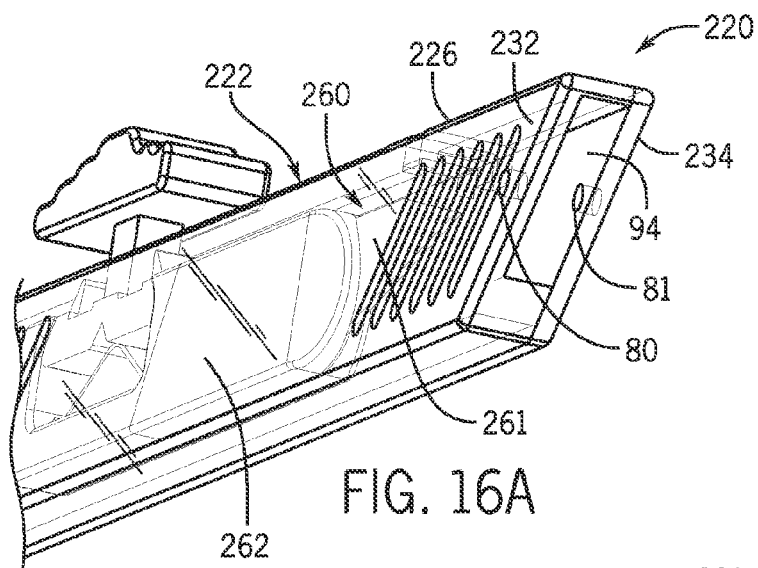
FIGS. 16A-16C are perspective views of a structure being inserted through holes in the long-handled scalpel of FIG. 14A.
Figure 16B:
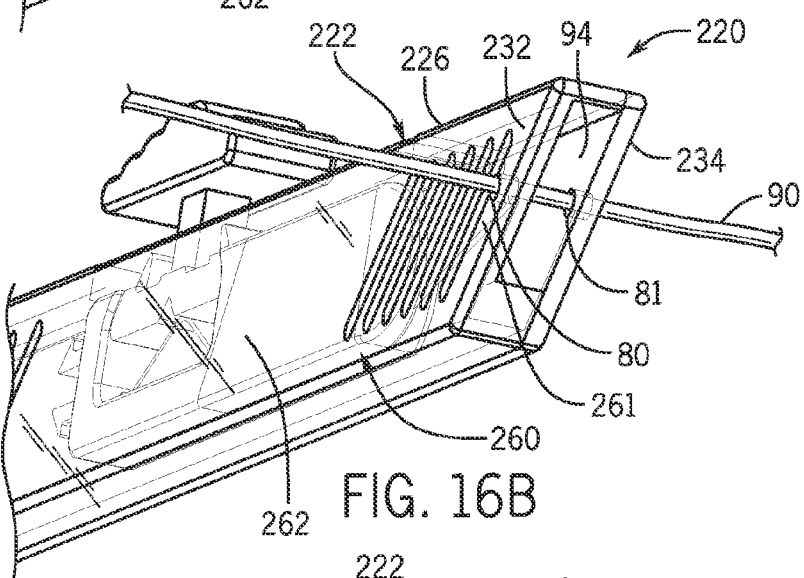
Figure 16C:
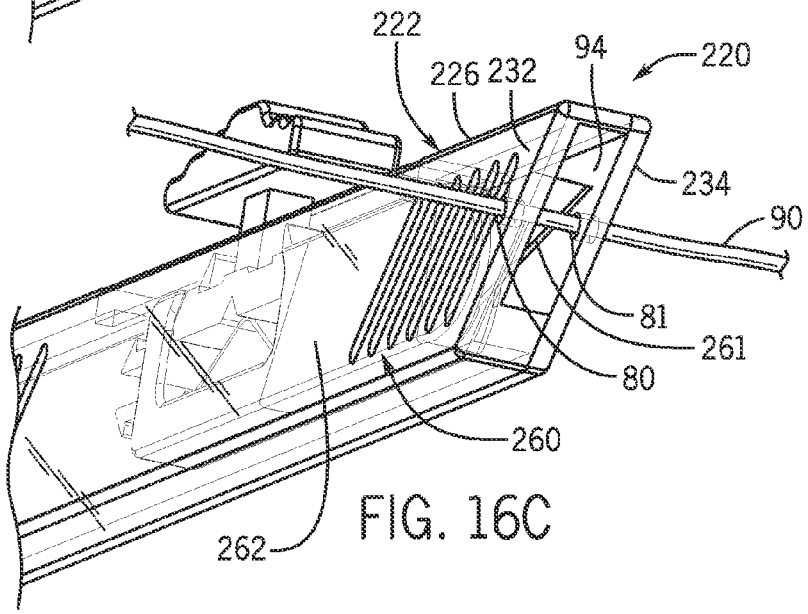

As shown in FIGS. 16A-16C, in order to secure the structure 90 in place, the first or front side 232 of the scalpel 220 may have a first hole 80 and the second or back side 234 of the scalpel 220 may include a second hole 81. The holes 80 and 81 may be positioned on a portion of the shaft 226 that is within the extension region 96 of the blade 261. The extension region 96 may refer to an area along the length of the blade cover 222 that the blade 261 moves within between the stowed position 52 and the use position 54. The first hole 80 and the second hole 81 may be aligned and disposed on a common center axis to allow the structure 90 to extend through both holes 80 and 81. The common center axis may extend through the center of the holes 80 and 81 and along the length of the holes 80 and 81. The common center axis of the holes 80 and 81 may be substantially perpendicular to the longitudinal axis of the blade body 260 and intersect with a path of movement or the extension region 96 of the blade 261. Accordingly, when the structure 90 is extended through the holes 80 and 81, the blade 261 intersects with and cuts the structure 90 as the blade body 260 is moved or extended toward the extended or use position.

FIGS. 16-17 depict the structure 90 being cut by the scalpel 220. As shown in FIGS. 16B and 17A, the structure 90 may be extended through and positioned within both holes 80 and 81 (e.g., the structure 90 may be aligned along the center axis of the holes 80 and 81) while the pusher 240 and the blade body 260 are retracted (e.g., in the stowed position). As the blade body 260 is extended along the shaft 226 toward the use position (as shown in FIGS. 16C and 17B), the blade 261 may intersect with the structure 90, thereby cutting or slicing through the structure 90 within the shaft 226. FIG. 17C shows the structure 90 cut into two pieces after the blade body 260 was been extended toward the use position when the structure 90 was been positioned within the holes 80 and 81. The scalpel 220 may subsequently be extended into the use position and used as a scalpel or retracted back into a stowed position.

The scalpel 20 or 220 may include multiple holes 80 and 81 on each side of the scalpel 20 or 220, according to the desired use. For example, it may be beneficial to have holes 80 and 81 with different sizes in order to securely hold a variety of differently sized structures 90. As shown in FIGS. 13A-13B, 15, and 19, each side of the blade covers 22 or 222 may have two holes (e.g., a small hole 82 and a large hole 84) with two different diameters and positions. However, it is anticipated that the scalpels 20 or 220 may have any number of holes 80 and 81.

The holes 80 and 81 may be a variety of different sizes and shapes, according to the desired configuration. For example, as shown in FIG. 13A-13B, the holes 80 and 81 may be circular. In order to allow the structure 90 to enter through the holes 80 and 81 more easily, the holes 80 and 81 may include a chamfer around the edges and on both sides of the holes 80 and 81. According to one embodiment, the chamfer may have a thickness between 0.5 to 0.75 mm thick and an angle between 25 to 65 degrees. According to another embodiment, the chamfer may be approximately 0.635 mm thick and have an angle of approximately 45 degrees.

The holes 80 and 81 may have a variety of different diameters according to the desired configuration. For example, according to one embodiment, the diameter of the holes 80 and 81 may be between 0.5 and 3 mm. According to another embodiment, the diameter of the holes 80 and 81 may be between 1 and 2.5 mm. According to yet another embodiment, the diameter of the holes 80 and 81 may be approximately 1.5 mm or 2 mm.

The holes 80 and 81 may be located anywhere on the scalpel 20 or 220 along the extension region 96 of the blade 61 or 261. According to one embodiment as shown in FIG. 13A, the holes 80 and 81 may be located toward the open end 94 of the scalpel 220 (the open end 94 may be the end of the scalpel 220 that the blade 261 extends out from the blade cover 222). For example, the holes 80 and 81 may be located 0.5 to 6 mm from the open end 94 of the scalpel 220. According to another embodiment, the holes 80 and 81 may be located from 1 to 5 mm from the open end 94 of the scalpel 220. According to yet another embodiment, the center of the holes 80 and 81 may be located approximately 1.5 or 4.5 mm from the open end 94 of the scalpel 220.

Additionally, the holes 80 and 81 may be located anywhere along the height (along the z-axis) of the scalpel 20 or 220. For example, the holes 80 and 81 may be located 6.5 to 9 mm from the bottom edge of the scalpel 20 or 220. According to another embodiment, the holes 80 and 81 may be located from 7 to 8.5 mm from the bottom edge of the scalpel 20 or 220. According to yet another embodiment, the center of the holes 80 and 81 may be located approximately 7.4 or 8.1 mm from the bottom edge of the scalpel 20 or 220.

The long-handled scalpel 220 may have a longer length than the mini scalpel 20, according to the desired configuration and use. The long-handled scalpel 220 may include a range of sizes according to the desired configuration. For example, preferably, the length of the blade cover 222 of the long-handled scalpel 220 may be between 9 and 15 cm. More preferably, the blade cover 222 of the long-handled scalpel 220 may have a length between 10 and 13 cm. Most preferably, the length of the blade cover 222 of the long-handled scalpel 220 may be approximately 12.2 cm. However, it is anticipated that the long-handled scalpel 220 may include a variety of dimensions according to the desired configuration.

Blade Cover

According to one embodiment as shown in FIGS. 1-5, the blade cover 22 may be opaque or not see-through. According to another embodiment as shown in FIGS. 14-19, the blade cover 22 or 222 (including the handle 24 or 224 and/or the shaft 26 or 226) may be clear, transparent, translucent, or see-through to allow the mechanisms within the scalpel 20 or 220 to be viewed. Accordingly, the blade body 60 or 260 may be viewed through the blade cover 22 or 222, allowing the user to know the exact location of the blade 61 or 261 at all times and increasing the safety of the scalpel 20 or 220. The color of the blade carrier 62 or 262 and/or the blade 61 or 261 may denote or indicate the size or type of the blade 61 or 261.

The embodiments disclosed herein allow the blade body of a mini scalpel to be locked into three different positions within the blade cover. Additionally, the embodiments disclosed herein allow a structure, such as a catheter, to be cut through the blade cover of the scalpel. Besides those embodiments depicted in the figures and described in the above description, other embodiments of the present invention are also contemplated. For example, any single feature of one embodiment of the present invention may be used in any other embodiment of the present invention.

Given the disclosure of the present invention, one versed in the art would appreciate that there may be other embodiments and modifications within the scope and spirit of the invention. Accordingly, all modifications attainable by one versed in the art from the present invention within the scope and spirit of the present invention are to be included as further embodiments of the present invention.

What is claimed is:

1. A safety scalpel comprising:
   a blade cover including a housing having a first side with a first hole and a second side with a second hole; and
   a blade body having a blade carrier and a blade,
   wherein the blade body is fully retractable and movable within the housing along a longitudinal axis,
   wherein the first hole and the second hole are disposed on a common center axis that is substantially perpendicular to the longitudinal axis of the blade body and intersects with a path of movement of the blade such that the blade is configured to cut a structure extending through the first and second holes as the blade is extended toward a use position.

2. The safety scalpel of claim 1, wherein the blade cover further includes a front lock member, a back lock member, and a safety lock member, wherein the front lock member, the back lock member, and the safety lock member are configured to define at least three different locked positions of the blade body relative to the housing.

3. The safety scalpel of claim 2, wherein the three different locked positions include the use position in which the blade is exposed outside of the housing, a stowed position in which the blade is fully concealed within the housing, and a safety position in which the blade is fully concealed within the housing and is retracted further into the housing than the stowed position.

4. The safety scalpel of claim 3, further comprising a pusher extending from outside of the housing into the housing, wherein the pusher is configured to cooperate with the front lock member and the back lock member to lock the blade body to the blade cover in the use position and the stowed position, respectively, wherein movement of the blade body corresponds to movement of the pusher.

5. The safety scalpel of claim 4, wherein the pusher includes a first hook and a second hook, wherein the first hook is configured to engage the front lock member to lock the blade body to the blade cover in the use position, and the second hook is configured to engage the back lock member to lock the blade body to the blade cover in the stowed position.

6. The safety scalpel of claim 3, wherein the blade body includes at least one safety hook along an end of the blade body opposite the blade, wherein the safety hook is configured to cooperate with the safety lock member to lock the blade body to the blade cover in the safety position.

7. The safety scalpel of claim 1, wherein the housing is transparent.

* * * * *